(12) United States Patent
Samulski et al.

(10) Patent No.: US 6,627,617 B1
(45) Date of Patent: Sep. 30, 2003

(54) TEMPERATURE-SENSITIVE REGULATION OF VIRAL VECTOR PRODUCTION

(75) Inventors: Richard Jude Samulski, Chapel Hill, NC (US); Denise Gavin, Silver Spring, MD (US); Nicholas Muzyczka, Gainesville, FL (US); Corinne Abernathy, Gainesville, FL (US); Daniel Pereira, Alexandria, VA (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/676,726

(22) Filed: Sep. 29, 2000

Related U.S. Application Data

(60) Provisional application No. 60/157,245, filed on Oct. 1, 1999, and provisional application No. 60/157,248, filed on Oct. 1, 1999.

(51) Int. Cl.$^7$ .................. C12N 15/63; C12N 15/00; A61K 39/23

(52) U.S. Cl. .................. 514/44; 424/233.1; 435/320.1; 435/235.1; 435/325

(58) Field of Search .................. 424/233.1; 435/320.1, 435/235.1, 325; 514/44

(56) References Cited

U.S. PATENT DOCUMENTS

| | | | |
|---|---|---|---|
| 5,139,941 A | 8/1992 | Muzyczka et al. | 435/172.3 |
| 5,589,377 A | 12/1996 | Lebkowski et al. | 435/240.2 |
| 5,691,176 A | 11/1997 | Lebkowski et al. | 435/172.3 |
| 5,773,289 A | 6/1998 | Samulski et al. | 435/320.1 |
| 5,837,484 A | 11/1998 | Trempe et al. | 435/69.1 |
| 5,856,152 A | 1/1999 | Wilson et al. | 435/172.3 |
| 5,858,775 A | 1/1999 | Johnson | 435/320.1 |
| 5,871,982 A | 2/1999 | Wilson et al. | 435/172.3 |
| 5,965,441 A | 10/1999 | Breakefield et al. | 435/456 |
| 6,037,177 A | 3/2000 | Snyder | 435/455 |
| 6,040,183 A | 3/2000 | Ferrari et al. | 435/457 |
| 6,063,627 A | 5/2000 | Mc Vey et al. | 435/440 |
| 6,086,913 A | 7/2000 | Tam et al. | 424/450 |
| 6,093,570 A | 7/2000 | Ferrari et al. | 435/457 |

FOREIGN PATENT DOCUMENTS

| | | | |
|---|---|---|---|
| WO | WO 98/32870 | 7/1998 | ........... C12N/15/86 |
| WO | WO 99/32647 | 7/1999 | ........... C12N/15/86 |
| WO | WO 99/53084 | 10/1999 | ........... C12N/15/86 |
| WO | WO 99/61601 | 12/1999 | ........... C12N/15/00 |
| WO | WO 00/01834 | 1/2000 | ........... C12N/15/86 |
| WO | WO 00/11149 | 3/2000 | ........... C12N/15/00 |
| WO | WO 00/17377 | 3/2000 | ........... C12N/15/86 |
| WO | WO 00/28061 | 5/2000 | ........... C12N/15/86 |
| WO | WO 00/55342 | 9/2000 | ........... C12N/15/86 |

OTHER PUBLICATIONS

Franklin, J. et al., Journal of Molecular Biology (1998) 277, 541–557.*

Chiorini, J. A., Kim, F., Yang, L., and Kotin, R. M. (1999). Cloning and characterization of adeno–associated virus type 5. *J.Virol.* 73, 1309–1319.

Clark, K. R., Voulgaropoulou, F., Fraley, D. M., and Johnson, P. R. (1995). Cell lines for the production of recombinant adeno–associated virus. *Hum.Gene Ther.* 6, 1329–1341.

Clark, K. R., Voulgaropoulou, F., and Johnson, P. R. (1996). A stable cell line carrying adenovirus–inducible rep and cap genes allows for infectivity titration of adeno–associated virus vectors. *Gene Ther.* 3, 1124–1132.

Conway, J. E., Rhys, C. M., Zolotukhin, I., Zolotukhin, S., Muzyczka, N., Hayward, G. S., and Byrne, B. J. (1999). High–titer recombinant adeno–associated virus production utilizing a recombinant herpes simplex virus type I vector expressing AAV–2 Rep and Cap. *Gene Ther.* 6, 986–993.

Davis, M. D., Wonderling, R. S., Walker, S. L., and Owens, R. A. (1999). Analysis of the effects of charge cluster mutations in adeno–associated virus Rep68 protein in vitro. *J.Virol.* 73, 2084–2093.

Ferrari, F. K., Xiao, X., McCarty, D., and Samulski, R. J. (1997). New developments in the generation of Ad–free, high–titer rAAV gene therapy vectors. *Nat.Med.* 3, 1295–1297.

Gavin, D. K., Young, S. M., Jr., Xiao, W., Temple, B., Abernathy, C. R., Pereira, D. J., Muzyczka, N., and Samulski, R. J. (1999). Charge–to–alanine mutagenesis of the adeno–associated virus type 2 Rep78/68 proteins yields temperature–sensitive and magnesium–dependent variants [published erratum appears in J Virol Jan. 2000;74(1):591]. *J.Virol.* 73, 9433–9445.

(List continued on next page.)

*Primary Examiner*—James Housel
*Assistant Examiner*—Stacy Brown
(74) *Attorney, Agent, or Firm*—Myers Bigel Sibley & Sajovec, P.A.

(57) ABSTRACT

The present invention provides temperature-sensitive (ts) adeno-associated virus (AAV) Rep78 and Rep68 proteins. In preferred embodiments, the ts AAV Rep78 and Rep68 proteins have missense mutations at amino acid positions 40, 42 and 44 that confer a temperature-sensitive phenotype. Also provided are nucleotide sequences and vectors encoding the inventive ts Rep proteins. In preferred embodiments, a hybrid adenovirus vector is provided that stably comprises a nucleotide sequence encoding a ts AAV Rep protein according to the invention. The present invention also provides methods of packaging AAV vectors and methods of ex vivo gene delivery using the ts Rep proteins of the invention. Further provided are cells containing the ts AAV Rep proteins, preferably stably integrated into the genome of the cell.

42 Claims, 7 Drawing Sheets

OTHER PUBLICATIONS

Johnston, K. M., Jacoby, D., Pechan, P. A., Fraefel, C., Borghesani, P., Schuback, D., Dunn, R. J., Smith, F. I., and Breakefield, X. O. (1997). HSV/AAV hybrid amplicon vectors extend transgene expression in human glioma cells. *Hum.Gene Ther.* 8, 359–370.

Li, J., Samulski, R. J., and Xiao, X. (1997). Role for highly regulated rep gene expression in adeno–associated virus vector production. *J.Virol.* 71, 5236–5243.

Palombo, F., Monciotti, A., Recchia, A., Cortese, R., Ciliberto, G., and La Monica, N. (1998). Site–specific integration in mammalian cells mediated by a new hybrid baculovirus–adeno–associated virus vector. *J.Virol.* 72, 5025–5034.

Pieroni, L., Fipaldini, C., Monciotti, A., Cimini, D., Sgura, A., Fattori, E., Epifano, O., Cortese, R., Palombo, F., and La Monica, N. (1998). Targeted integration of adeno–associated virus–derived plasmids in transfected human cells. *Virology* 249, 249–259.

Recchia, A., Parks, R. J., Lamartina, S., Toniatti, C., Pieroni, L., Palombo, F., Ciliberto, G., Graham, F. L., Cortese, R., La Monica, N., and Colloca, S. (1999). Site–specific integration mediated by a hybrid adenovirus/adeno– associated virus vector. *Proc.Natl.Acad.Sci.U.S.A* 96, 2615–2620.

Rhode, S. L., III (1978). Replication process of the parvovirus H–1. X. Isolation of a mutant defective in replicative-form DNA replication. *J.Virol.* 25, 215–223.

Rizzuto, G., Gorgoni, B. Cappelletti, M., Lazzaro, D., Gloaguen, I., Poli, V., Sgura, A., Cimini, D., Ciliberto, G., Cortese, R., Fattori, E., and La Monica, N. (1999). Development of animal models for adeno–associated virus site–specific integration. *J.Virol.* 73, 2517–2526.

Urabe, M.,, Hasumi, Y., Kume, A., Surosky, R. T., Kurtzman, G. J., Tobita, K., and Ozawa, K. (1999). Charged-to–alanine scanning mutagenesis of the N–terminal half of adeno– associated virus type 2 Rep78 protein. *J.Virol.* 73, 2682–2693.

Vincent, A. J., Esandi, M. C., Avezaat, C. J., Vecht, C. J., Sillevis, S. P., van Bekkum, D. W., Valerio, D., Hoogerbrugge, P. M., and Bout, A. (1997). Preclinical testing of recombinant adenoviral herpes simplex virus– thymidine kinase gene therapy for central nervous system malignancies. *Neurosurgery* 41, 442–451.

Walker, S. L., Wonderling, R. S., and Owens, R. A. (1997). Mutational analysis of the adeno–associated virus type 2 Rep68 protein helicase motifs. *J.Virol.* 71, 6996–7004.

Walker, S. L., Wonderling, R. S., and Owens, R. A. (1997). Mutational analysis of the adeno–associated virus Rep68 protein: identification of critical residues necessary for site–specific endonuclease activity. *J.Virol.* 71, 2722–2730.

Wonderling, R. S., Kyostio, S. R., and Owens, R. A. (1995). A maltose–binding protein/adeno–associated virus Rep68 fusion protein has DNA–RNA helicase and ATPase activities. *J.Virol.* 69, 3542–3548.

Bowie, J.U., Reidharr–Olson, J.F., Lim, W.A., Sauer, R.T. (1990). Deciphering the Message in Protein Sequences: Tolerance to Amino Acid Substitutions. *Science.* 247, 1306–1310.

Rudinger, J. (1976). Characteristics of the amino acids as components of a peptide hormone sequence. *Baltimore University Park Press.* 5–7.

Thomson, B.J., Weindler, F.W., Gray, D., Schwabb, V., Heilbronn. R. (1994). Human Herpesvirus (JJV–6) is a helper virus for Adeno–Associated Virus Type 2 (AAV–2) and the AAV–2 rep gene homologue in HHV–6 can mediate AAV–2 DNA replication and regulate gene expression. *Virology.* 204, 304–311.

Wang, X.S., Qing, K., Ponnazhagan, S., Srivastava, A. (1997). Adeno–Associated Virus Type 2 DNA replication in vivo; mutation analyses of the D sequence in viral onverted terminal repeats. *Journal of Virology.* 72, 3077–3082.

Wicker, R.,Gunther, M. (1988). Isolation and characterization of thermosensitive mutants from Kilham Rat Virus, a rodent papvovirus. *Journal of General Virology.* 69, 163–175.

Yang, Q., Kadam. A., Trempe, J.T. (1992). Mutational analysis of the adeno–associated virus rep gene. *Journal of Virology.* 65, 6058–6059.

Copy of PCT Search Report for corresponding application PCT/US00/26916.

* cited by examiner

B.

C.

A.

B.

C.

A.

B.

C.

SEQUENCE LISTING

<160> NUMBER OF SEQ ID NOS: 1

<210> SEQ ID NO 1
<211> LENGTH: 27
<212> TYPE: DNA
<213> ORGANISM: synthetic construct

<400> SEQUENCE: 1
ccgccagctt ctgccatggc tctgaat                27

TEMPERATURE-SENSITIVE REGULATION OF VIRAL VECTOR PRODUCTION

RELATED APPLICATION INFORMATION

This application claims the benefit of United States Provisional Application No. 60/157,245, filed Oct. 1, 1999, and United States Provisional Application No. 60/157,248, filed Oct. 1, 1999, which are incorporated by reference herein in their entirety.

STATEMENT OF FEDERAL SUPPORT

This invention was made, in part, with government support under grant numbers 2-RO1-HL048347, RO1 GM35723, PO1 HL59412, and PO1 NS36302 from the National Institutes of Health. The United States government has certain rights to this invention.

FIELD OF THE INVENTION

The present invention pertains to reagents and methods for producing virus vectors, in particular, reagents and methods for producing adeno-associated virus vectors.

BACKGROUND OF THE INVENTION

Adeno-associated virus (AAV) type 2 is a nonpathogenic human parvovirus that generally depends on coinfection with a helper virus (adenovirus or herpesvirus) for efficient replication (reviewed in Berns (1996). Parvoviridae: The viruses and their replication, p. 2173–2197, in B. N. Fields (ed.), Fields Virology, 3$^{rd}$ ed., vol. 2, Raven, Philadelphia). The linear, single-stranded DNA genome of AAV encodes two open reading frames (rep and cap) flanked by 145 bp inverted terminal repeats (ITR) (Srivastava et al., (1983) *J. Virol.* 45:555). Replication of the AAV genome requires two viral components, the ITR that serves as the origin of replication (Hauswirth et al., (1977) *Virology* 78:488; Straus et al., (1976) *Proc. Natl. Acad. Sci. USA* 73:742; Samulski et al., (1983) *Cell* 33:135; Senepathy et al., (1984) *J. Mol. Biol.* 179:1) and the rep gene products (Senepathy et al., (1984) *J. Mol. Biol.* 179:1, Hermonat et al., (1984) *J. Virology* 51:329; Tratschin et al., (1984) *J. Virology* 51:611). The rep gene encodes four multifunctional proteins (Hermonat et al., (1984) *J. Virology* 51:329; Tratschin et al., (1984) *J. Virology* 51:611; Mendelson et al., (1986) *J. Virology* 60:823; Trempe et al., (1987) *Virology* 161:18) that are expressed from two promoters at map units 5 (p5) and 19 (p19). The larger Rep proteins transcribed from the p5 promoter (Rep78 and Rep68), are essentially identical except for unique carboxy termini generated from unspliced (Rep78) and spliced (Rep68) transcripts, respectively (Srivastava et al, (9183) *J. Virol.* 45:555). Two smaller rep proteins (Rep52, Rep40), transcribed from the p19 promoter are amino terminal truncations of Rep78 and Rep68, respectively.

Several biochemical activities of Rep78 and Rep68 have been characterized as necessary for AAV replication. These include specific binding to the AAV ITR (Ashktorab et al., (1989) *J. Virology* 63:3034; Im et al., 1989) *J. Virology* 63:3095; Snyder et al., (1993) *J. Virology* 67:6096) and site-specific endonuclease cleavage at the terminal resolution site (trs) (Im et al., (1990) *J. Virology* 63:447; Im et al., (1992) *J. Virology* 66:1119; Snyder et al., (1990) *Cell* 60:105; Snyder et al., (1990) *J. Virology* 64:6204). Rep78/68 also possess ATP dependent DNA-DNA helicase ((Im et al., (1990) *J. Virology* 63:447; Im et al., (1992) *J. Virology* 66:1119) and DNA-RNA helicase as well as ATPase activities (Wonderling et al., (1995) *J. Virology* 69:3542). In addition to these activities required for replication, Rep78/68 also regulate transcription from the viral promoters (Beaton et al., (1989) *J. Virology* 63:4450; Labow et al., (1986) *J. Virology* 60:251; Tratschin et al., (1986) *Mol. Cellular Biol.* 6:2884; Kyostio et al., (1994) *J. Virology* 68:2947; Pereira et al., (1997) *J. Virology* 71:1079), and have been shown to mediate viral targeted integration (Xiao, W., (1996), "Characterization of cis and trans elements essential for the targeted integration of recombinant adeno-associated virus plasmid vectors", Ph.D. Dissertation, University of North Carolina-Chapel Hill; Balague et al., (1997) *J. Virology* 71:3299; LaMartina et al., (1998) *J. Virology* 72:7653; Pieroni et al., (1998) *Virology* 249:249).

Mutant studies of the Rep proteins have indicated that the activities of Rep can be divided into partially distinct functional domains (FIG. 1A) that are spread throughout the protein (Chejanovsky et al., (1989) *Virology* 173:120; McCarty et al., (1992) *J. Virology* 66:4050; Yang et al., (1992) *J. Virology* 66;6058; Owens et al., (1993) *J. Virology* 67:997; Weitzman et al., (1996) *J. Virology* 70:2440; Walker et al., (1997) *J. Virology* 71:2722; Walker et al., (1997) *J. Virology* 71:6996; Davis et al., (1999) *J. Virology* 73:2084; Urabe et al., (1999) *J. Virology* 73:2682). These include regions required for binding to the ITR; a putative NTP-binding/ATPase domain, nuclear localization and residues putatively required for nicking and helicase functions. Several mutations within the NTP-binding/ATPase domain that lacked trs endonuclease and viral replication were also defective for trans-activation functions suggesting a need for further mutant analysis (McCarty et al., (1992) *J. Virology* 66:4050). Since most mutants disrupt multiple Rep mediated functions for the AAV life cycle, detailed characterization of distinct functions has been difficult (McCarty et al., (1992) *J. Virology* 66:4050; Yang et al., (1992) *J. Virology* 66:6058; Owens et al., (1993) *J. Virology* 67:997; Weitzman et al., (1996) *J. Virology* 70:2440; Walker et al., (1997) *J. Virology* 71:2722; Walker et al., (1997) *J. Virology* 71:6996; Davis et al., (1999) *J. Virology* 73:2084; Urabe et al., (1999) *J. Virology* 73:2682).

One of the considerations in designing methods for production or delivery of AAV is the toxicity of the AAV Rep proteins to helper viruses (e.g., adenovirus). Thus the AAV rep/cap genes are typically provided on a separate vector from the helper virus or silenced in the cell chromosome. In addition, the rep gene products are frequently cytotoxic to the cells used to package rAAV vectors.

The use of temperature sensitive (ts) mutations has proven to be an effective method for elucidating the essential functions of viral proteins (Murphy et al., (1988) *Virus Research* 11:1; Crowe et al., (1996) *Virus Genes* 13:269; Rhode (1978) *J. Virology* 25:215; Burns et al., (1992) *Virology* 189:568). One approach for generating ts mutants has been to utilize the charged-to-alanine mutagenesis strategy (Cunningham et al., (1989) *Science* 244:1081; Bennett et al., (1991) *J. Biological Chemistry* 266:5191; Bass et al., (1991) *Proc. Nat. Acad. Sci. USA* 88:4498; Wertman et al., (1992) *Genetics* 132:337; Diamond et al., (1994) *J. Virology* 68:863; Parkin et al., (1996) *Virus Research* 46:31). The rationale of this approach is that since most charged residues are found on the protein surface they are expected to exert little effect on protein folding or stability (Cunningham et al., (1989) *Science* 244:1081; Wertman et al., (1992) *Genetics* 132:337; Dao-Pin et al., (1991) *Biochemistry* 30:11521), but could feasibly make a protein more thermosensitive by disrupting electrostatic and H-bonding interactions (Diamond et al., (1994) *J. Virology* 68:863). This technique does not always yield ts proteins, but is a popular approach when the crystal structure of the protein in question is lacking.

Accordingly, ts AAV Rep mutants would be advantageous to provide a functional Rep protein that may be controlled or inactivated at non-permissive temperatures so that the toxicity normally associated with AAV Rep proteins may be diminished or avoided.

SUMMARY OF THE INVENTION

The present invention addresses a need in the art for improved strategies for producing AAV vectors. In addition, the present invention is directed to a need in the art for improved reagents and methods for gene delivery.

Current techniques for packaging AAV vectors are not readily amenable to large-scale production. These difficulties arise, in part, from toxicity of the AAV Rep proteins to helper viruses and host cells, thus requiring that the AAV rep/cap genes be provided on a separate vector from the helper virus or silenced in the cell chromosome. In addition, the rep gene products are frequently cytotoxic to the cells used to package rAAV vectors. The present invention provides temperature-sensitive (ts) AAV Rep proteins, and nucleotide sequences encoding the same, that may be used according to the methods disclosed herein to reduce or mitigate the problems posed by Rep protein toxicity. The activity of the inventive ts Rep proteins may be readily controlled by shifting the cells packaging the rAAV vectors to permissive or non-permissive temperatures as desired.

As one aspect, the present invention provides a ts AAV Rep protein. The ts Rep protein may be any of the AAV Rep proteins, but is preferably a ts Rep78 or Rep68 protein. Also preferred are heat sensitive AAV Rep proteins. The amino terminus of the large Rep proteins are associated with DNA binding and other activities. Accordingly, illustrative AAV Rep proteins of the invention comprise a mutation in the amino-terminal half thereof, wherein the mutation confers a temperature sensitive phenotype to the AAV Rep protein. In a further exemplary embodiment, the AAV Rep protein comprises a mutation selected from the group consisting of: (a) a mutation at amino acid position 40, (b) a mutation at amino acid position 42, (c) a mutation at amino acid position 44, and (d) combinations of (a)–(c), wherein the mutation confers a temperature sensitive phenotype to the AAV Rep protein.

The invention further provides destabilizing mutations in the AAV Rep sequences that increase the turnover rate of the protein. In illustrative embodiments, the destabilizing mutation is selected from the group consisting of: (a) a missense mutation at the p19 start site (i.e., the translation start site for the Rep52 and Rep40 proteins), (b) a missense mutation at the 5' splice donor site; and (c) a missense mutation at the p19 start site and 5' splice donor site. These mutations may be further advantageously combined with the inventive ts mutations to provide another level of control over Rep activity.

As a further aspect, the present invention provides a nucleotide sequence encoding the inventive ts sensitive AAV Rep protein(s). In particular preferred embodiments, the sequence encodes both a ts AAV Rep78 protein and a temperature-sensitive AAV Rep68 protein. The nucleotide sequence may further encode the AAV Rep52 protein and/or an AAV Rep40 protein, which may also have a ts phenotype. In one particular embodiment, the invention provides a nucleotide encoding a ts Rep protein, wherein the nucleotide sequence comprises: (a) rep coding sequences encoding a temperature-sensitive AAV Rep78 protein and a temperature sensitive Rep68 protein, and (b) a rAAV template comprising a heterologous nucleotide sequence flanked by 5' and 3' AAV inverted terminal repeats, wherein the rep coding sequence is not flanked by the AAV inverted terminal repeats.

As another aspect, the present invention provides an AAV Rep protein comprising a mutation at amino acid position 412, wherein the AAV Rep protein is an AAV Rep78 or AAV Rep68 protein, and wherein the mutation results in a reduced (e.g., diminished or decreased) affinity of the AAV Rep protein for magnesium (e.g., at least about a 33%, 50%, 75%, 90%, 95% reduction or more). This mutant Rep protein may be regulated by modulating magnesium concentrations. This Rep protein also finds use for investigating the structure of the Rep protein magnesium pocket and the effects of magnesium concentration on Rep activity.

As a further aspect, the present invention provides a hybrid adenovirus or herpesvirus vector stably expressing a ts AAV Rep78 or ts Rep68 protein. Rep protein interference with the helper virus may be avoided at non-permissive temperatures. In other preferred embodiments, the hybrid helper virus expresses the AAV cap and rep genes, wherein the rep genes encode a ts AAV Rep78 and/or AAV Rep68 protein. In still other preferred embodiments, the adenovirus vector further comprises a rAAV template comprising a heterologous nucleotide sequence and an AAV inverted terminal repeat. This vector may be used to provide all of the functions necessary to package rAAV particles on a single construct.

As another preferred embodiment, the invention provides a hybrid adenovirus vector, comprising, in an adenovirus backbone: (a) the adenovirus 5' and 3' sequences sufficient for adenovirus replication and packaging; (b) AAV Rep coding sequences encoding a temperature-sensitive AAV Rep protein, wherein the AAV Rep protein is a Rep78 or Rep68 protein, and wherein the AAV Rep coding sequences are flanked by the adenoviral sequences of (a).

These hybrid helper vectors may be introduced into packaging cells along with a rAAV vector template (e.g., carried by a plasmid, viral vector, or embedded in the chromosomal DNA) to produce rAAV vectors. The hybrid vector may be amplified to produce a large-scale stock, and the stock used to infect a packaging cell in the presence of a rAAV template at the permissive temperature to induce AAV vector replication and packaging. In another preferred embodiment, the AAV vector is provided as a rAAV virus. Propagation of the hybrid helper virus and rAAV vector template as two viruses within a permissive cell provides rapid amplification of both the rAAV vector and the packaging machinery within the cell.

Accordingly, in one particular embodiment, the invention provides a method of producing a rAAV particle, comprising providing to a cell permissive for AAV replication: (a) a rAAV template comprising a (i) heterologous nucleotide sequence, and (ii) AAV packaging signal sequences sufficient for the encapsidation of the AAV template into infectious rAAV particles; and (b) AAV sequences sufficient for replication and packaging of the AAV template into infectious viral particles, wherein the AAV sequences encode a temperature sensitive AAV Rep protein, wherein the AAV Rep protein is a Rep78 or Rep68 protein; under conditions permissive for the temperature-sensitive AAV Rep protein and sufficient for the replication and packaging of the rAAV template, whereby infectious rAAV particles comprising the rAAV template are produced in the cell. The method may further comprise the step of collecting the infectious rAAV particles, e.g., from the medium and/or by lysing the cells. In particular embodiments, the method further comprises providing helper virus sequences which provide the helper virus functions essential for a productive AAV infection, wherein the helper virus sequences cannot be packaged into infectious rAAV viral particles. It is further preferred that the AAV replication and packaging sequences cannot be packaged into infectious rAAV viral particles.

As still a further aspect, the present invention provides improved methods of ex vivo gene delivery using AAV vectors. AAV is the only viral vector known to integrate at a specific target locus within the chromosome. Targeted integration is mediated by the Rep78 and/or Rep68 proteins. This unique attribute of AAV vectors has not been extensively utilized because the Rep proteins are absent from essentially all current ex vivo and in vivo gene therapy protocols. According to the present invention, the ts AAV Rep78 and/or Rep68 proteins are used to mediate targeted integration of AAV vectors in cells ex vivo at permissive temperatures. The cells may then be shifted to non-permissive temperatures to inactivate the ts Rep protein(s), thereby mitigating concerns regarding the presence of functional Rep protein in target cells as well as potential toxicity to target cells. The cells may then be administered to a subject in vivo, e.g., to produce a therapeutic or immunogenic response in the subject.

In one embodiment, the invention provides a method of integrating a nucleotide sequence into a chromosome of a cell, comprising: providing a nucleotide sequence to a cell, wherein the nucleotide sequence comprises a recombinant AAV template comprising (a) AAV sequences sufficient for integration of the AAV template into the cell, and (b) a heterologous nucleotide sequence, and providing a temperature-sensitive AAV Rep protein(s) to the cell, wherein the nucleotide sequence and the temperature-sensitive AAV Rep protein are provided under conditions permissive for the temperature-sensitive AAV Rep protein, whereby the recombinant AAV template is integrated into a chromosome of the cell.

In a further aspect of the invention, the modified cell is administered to a subject. In one particular embodiment, the invention provides a method of administering a nucleotide sequence to a subject, comprising: (a) providing a nucleotide sequence to a cell, wherein the nucleotide sequence comprises a recombinant AAV template comprising (a) AAV sequences sufficient for integration of the AAV template into the cell, and (b) a heterologous nucleotide sequence; and (b) providing to the cell a temperature-sensitive AAV Rep protein; wherein the nucleotide sequence and the temperature-sensitive Rep protein are provided under conditions permissive for the temperature-sensitive AAV Rep protein, whereby the recombinant AAV template is integrated into a chromosome of the cell; and (c) administering the cell to a subject. The method may further comprise the step of shifting the cell to a non-permissive temperature prior to administering the cell to the subject.

In particularly preferred embodiments of the present invention, the ts AAV Rep78 and/or Rep68 protein is expressed from a vector construct that also comprises a rAAV template to be delivered to the target cell. The Rep protein(s) mediates the targeted integration of the rAAV vector into the chromosome at the permissive temperature, but the Rep protein(s) are not integrated. This embodiment also advantageously permits the delivery of relatively large heterologous nucleotide sequences, which would exceed the limited capacity of the AAV capsid (approximately 4.5 kb), between the AAV ITRs. Preferably, the rep coding sequences are not flanked by the AAV integration sequences (e.g., ITRs).

These and other aspects of the present invention are described in more detail in the description of the invention set forth below.

DETAILED DESCRIPTION OF THE INVENTION

Figure 1:
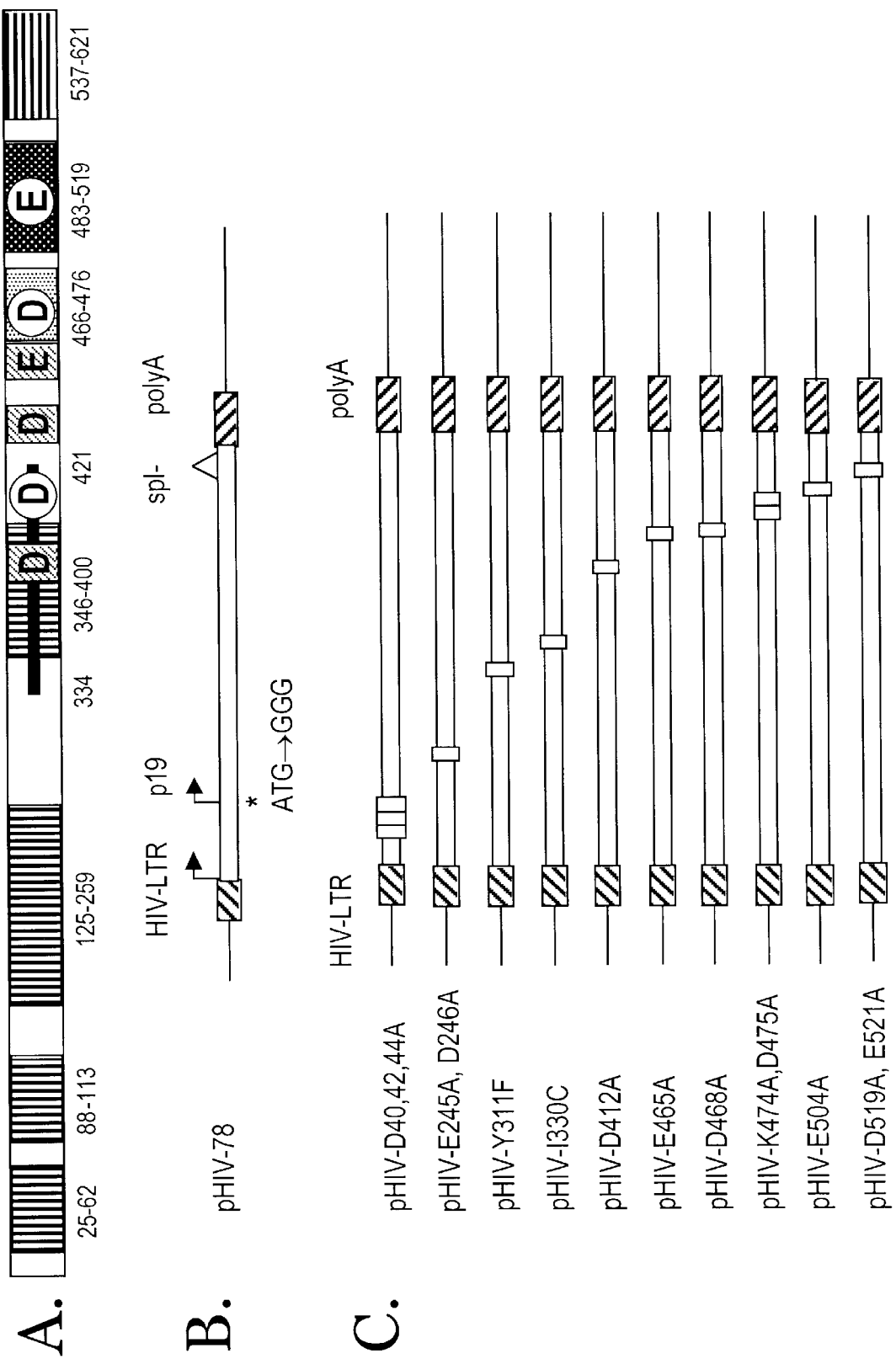
FIG. 1. AAV2 Rep78 protein. Panel A. Schematic diagram of putative functional domains within Rep78/68. Regions described as required for binding (vertical stripes), nuclear localization (black box, aa 483–519), oligomerization (gray box, aa 466–476), ATPase/helicase activity (black line, aa 334–412), and the unique region between Rep78 and Rep68 (horizontal stripes, aa 537–621) are indicated. Overlapping DD35E motifs are indicated as boxed residues corresponding to one motif at aa D368, D429, E465; and circled residues corresponding to a second motif at aa D412, D468, E504. Panel B. Eucaryotic expression cassette (pHIV-78) for generating Rep78 proteins. Protein expression is under control of the HIV-LTR promoter and the poly A signal from SV40. The initiation codon (ATG) at p19 was changed to GGG to eliminate expression of Rep52 and Rep40 and the splice donor site was modified (spl–) to eliminate expression of Rep68. Panel C. The position of point and clustered alanine mutations (open boxes) are indicated within the pHIV-78 expression plasmid. Amino acid changes are indicated by the nomenclature of each construct.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *PatentIn User Manual*, 99–102 (November 1990) (U.S. Patent and Trademark Office).

Except as otherwise indicated, standard methods may be used for the construction of rAAV vectors, helper vectors, and packaging cells according to the present invention. Such techniques are known to those skilled in the art (see e.g., SAMBROOK et al., Molecular Cloning: A Laboratory Manual 2d ed. (Cold. Spring Harbor, N.Y. 1989); F. M. Ausubel et al, Current Protocols in Molecular Biology (Green Publishing Associates, Inc. and John Wiley & Sons, Inc., New York).

The present invention is based, in part, on the discovery of temperature-sensitive (ts) adeno-associated virus (AAV) Rep proteins. These ts Rep proteins may be advantageously employed as novel reagents for improved methods of producing and/or delivering AAV vectors.

A significant problem in the development of AAV vectors for clinical applications (e.g., gene therapy) has been the difficulty of producing sufficient quantities of vector stocks (see, e.g., Samulski et al., Adeno-associated Viral Vectors, in The Development of Human Gene Therapy, ed., T.

Friedmann, Cold Spring Harbor Laboratory Press, Cold Spring Harbor, N.Y., 1999). The triple-transfection methods typically employed to produce AAV vectors are not easily modified for large-scale production. An additional limitation of AAV vectors has been the packaging constraints of the AAV capsid. The relatively small capacity of the AAV capsid places limits on the size of exogenous nucleotide sequences and/or expression control elements that may be efficiently delivered with an AAV vector (see, e.g., Samulski et al., Adeno-associated Viral Vectors, in The Development of Human Gene Therapy, ed., T. Friedmann, Cold Spring Harbor Laboratory Press, Cold Spring Harbor, N.Y., 1999; Chuah et al., (1998) *Critical Review in Oncology/ Hematology* 28:153). The wild-type AAV genome is approximately 4.6 kb in length, and Dong et al., (1996) *Human Gene Therapy* 7:2102, have reported that the efficiency of packaging rAAV genomes diminishes as the size increases over wild-type, with dramatic reductions observed with transgene cassettes over 4.9 kb (>105% of wild-type).

The present invention is of significance to the development of AAV vectors, in part, because it may address these long-term concerns in the art, while retaining the known advantages of AAV vectors (e.g., non-pathogenic, low or no host immune response, stable transgene expression, targeted integration, transduction of both dividing and non-dividing cells). The inventive reagents may be used in AAV production methods that are less cumbersome and more readily scalable than are current protocols. Furthermore, the present invention may enable the delivery of nucleic acid sequences that exceed the size limitations of currently-employed AAV vectors, in particular, in methods of ex vivo gene therapy.

As used herein, the term "AAV" refers to adenoassociated virus in both the wild-type and the recombinant form (rAAV) and encompasses mutant forms of AAV. The term AAV further includes, but is not limited to, AAV type 1, AAV type 2, AAV type 3, AAV type 4, AAV type 5, AAV type 6, avian AAV, bovine AAV, canine AAV, equine AAV, and ovine AAV (see, e.g., Bernard N. Fields et al., Virology, volume 2, chapter 69 (3d ed., Lippincott-Raven Publishers). In a preferred embodiment, the AAV used in the present invention is AAV type 2.

A rAAV vector is an AAV particle that comprises a heterologous (i.e., foreign) nucleotide sequence in its genome. rAAV vectors require only the 145 base terminal repeats in cis to generate virus. All other viral sequences are dispensable and may be supplied in trans (Muzyczka, (1992) *Curr. Topics Microbiol. Immunol.* 158:97). Typically, rAAV vectors will only retain the minimal terminal repeat sequences so as to maximize the size of the transgene that can be efficiently packaged by the vector.

Further, as described in more detail below, the AAV genome may be embedded in another delivery vector, e.g., a hybrid adenovirus/AAV vector or a hybrid herpesvirus/ AAV vector, as described below. Alternatively, the AAV vector may be a viral vector as described in WO 00/28004, the disclosure of which is incorporated by reference herein in its entirety.

As used herein, "transduction" or "infection" of a cell by AAV means that the AAV enters the cell to establish a latent or active (i.e., lytic) infection, respectively. See, e.g., Bernard N. Fields et al., Virology, volume 2, chapter 69 (3d ed., Lippincott-Raven Publishers). In embodiments of the invention in which the AAV is introduced into a cell for the purpose of delivering a nucleotide sequence to the cell, it is preferred that the AAV integrates into the genome and establishes a latent infection.

Temperature-Sensitive AAV Rep Proteins

The present investigations have resulted in the production of temperature-sensitive (ts) AAV Rep proteins. As described above, the AAV rep genes encode four AAV Rep proteins: Rep78, Rep68, Rep52 and Rep40. The Rep78 and Rep68 proteins are both expressed from the p5 promoter and only differ in the carboxyl-terminal region due to splicing of the Rep68 transcript. The smaller Rep52 and Rep40 proteins are transcribed from the p19 promoter and are amino terminal truncations of the Rep78 and Rep68 proteins, respectively.

As used herein, an "AAV Rep protein" may be an AAV Rep78, Rep68, Rep52 and/or Rep40 protein, but is preferably an AAV Rep78 and/or Rep68 protein. Due to the overlapping coding regions of the four Rep proteins, those skilled in the art will appreciate that a particular mutation(s) may affect more than one, or even all, of the AAV Rep proteins. Those skilled in the art will further appreciate that the claimed AAV Rep proteins may include modifications and/or mutations (including truncations) other than the inventive mutations described herein, as long as the usefulness of the resulting modified and/or mutated AAV Rep protein is not thereby abrogated.

The ts AAV Rep proteins may also contain covalent modifications, as long as the additional modification(s) does not unduly impair the activity of the Rep protein, thereby making it an unsuitable template for assessing the effects of other mutations on Rep function. (e.g., a His tag for purification purposes. The ts AAV Rep proteins may also be modified to contain a "nonclassical" import/export signal peptide (e.g., fibroblast growth factor-1 and -2, interleukin 1, HIV-1 Tat protein, herpes virus VP22 protein, and the like) for cellular delivery, as described by Cleves, (1997) *Current Biology* 7:R318. The AAV Rep proteins may also be tagged with peptide motifs that direct uptake by specific cells, as is known in the art, e.g., a FVFLP peptide motif triggers uptake by liver cells.

The ts AAV Rep mutants of the invention may be heat- or cold-sensitive, but are preferably heat-sensitive mutants.

As used herein, a "temperature-sensitive" AAV Rep protein exhibits a ts phenotype, as that term is understood in the art, for at least one Rep protein function (i.e., activity). In general, such proteins are non-naturally occurring and/or have not previously been isolated from nature. Typically, temperature-sensitive mutants selectively display the mutant phenotype at high or low temperatures. The mutation is generally only manifest in a limited temperature range. The ts protein generally functions normally, but is unstable at a restrictive or "non-permissive" temperature as described below. Thus, for a heat sensitive mutant, the protein shows a relatively normal phenotype at the lower (permissive) temperature, but when placed at a higher (non-permissive) temperature shows the mutant phenotype.

The AAV Rep proteins have many known functions including, but not limited to, DNA replication, integration, ATPase activity, DNA binding, helicase activity, and site- and strand-specific endonuclease activity. Some of these activities have been tentatively ascribed to individual Rep protein(s) and/or domains of the Rep protein(s). Accordingly, it will be understood by those skilled in the art that a particular mutation may not affect all aspects of Rep protein functioning. Preferably, the ts AAV Rep proteins of the present invention are temperature-sensitive for viral replication, DNA replication, DNA binding, site- and strand-specific endonuclease activity, helicase and/or integration. More preferably, the ts Rep proteins are temperature-sensitive for two or more of the foregoing Rep functions, most preferably, for all of the foregoing Rep functions.

The ts Rep proteins of the invention demonstrate an alteration, change or modification in at least one Rep function at non-permissive temperatures (preferably elevated temperatures).

As used herein, a "permissive" temperature is a temperature at which the ts Rep mutant displays essentially wild-type Rep activity. By "essentially wild type" Rep activity, it is intended that the ts Rep mutant demonstrates at least about 90%, 95% or even essentially 100% of the Rep activity of the wild-type Rep protein evaluated under similar conditions. Typically, "permissive" temperatures will be in the range of about 30° C. to about 35° C. For heat sensitive mutants, "permissive" temperatures will generally be less than about 35° C., preferably less than about 34° C., more preferably less than about 33° C.

As used herein, a "non-permissive" temperature is a temperature at which the ts Rep mutant displays the mutant phenotype for at least one Rep function, as described above. At "non-permissive" temperatures, the ts Rep mutant will exhibit a substantial reduction in at least one Rep activity as compared with the wild-type Rep protein evaluated under similar conditions. By "substantial reduction", it is meant that the ts Rep mutant will exhibit at least about a 33%, 50%, 75%, 90%, 95%, 99% or even more reduction in at least one Rep function (as described above) as compared with the wild-type Rep protein. In particular embodiments, the ts Rep protein may exhibit no detectable activity at non-permissive temperatures at which the wild-type protein still exhibits high levels of activity.

For heat sensitive mutants, "non-permissive" temperatures will generally be greater than about 34° C., greater than about 36° C., greater than about 37° C., greater than about 39° C., or even higher. Exemplary non-permissive temperatures are in the range of about 36° C. to about 40° C., more preferably about 37° C. to about 39° C.

It will be understood by those skilled in the art that all proteins will exhibit activity losses at sufficiently high or low temperatures (e.g., as a result of protein denaturation). However, the effects of temperature extremes will impact the wild-type Rep protein as well, and typically will not be selective only for the ts Rep protein.

Those skilled in the art will appreciate that ts mutants often exhibit a graded response as the temperature is elevated (or lowered). For example, the D40,42,44A-78 mutant described herein is permissive (although delayed) for replication at 32° C., exhibits an approximately 3–4 fold reduction in DNA replication activity at 37° C., and no detectable DNA replication activity at 39° C. Replication differences resulted in a 2-log and 3-log reduction in virus yields at 37° C. and 39° C., respectively, as compared with 32° C.

Thus, in preferred embodiments, at non-permissive temperatures, the ts AAV Rep proteins of the invention exhibit at least about a two, three, four, or even greater log reduction in viral replication as compared with the wild-type protein.

As described above, the ts Rep protein is preferably an AAV Rep 78 or AAV Rep 68 protein.

A phenotype that is only delayed, is not "reduced" according to the present invention. For example, one of the particular tsRep mutants described herein (D40,42,44A-78) exhibits a delayed replication phenotype at a permissive temperature of 32° C. as compared with wild-type, but exceeds wild-type replication activity by 48 hours. The term "delayed" as used herein does not include the low level of activity or "leakiness" that is observed even with substantially or essentially inactive protein mutants. Thus, typically, the inventive ts Rep proteins exhibit a reduction in the maximum level of at least one Rep protein function (as described above).

Rep function/activity can be determined by any method known in the art. For example, DNA binding is typically assessed by electrophoretic mobility shift assays (EMSA) to AAV terminal repeat hairpin DNA. Site- and strand-specific endonuclease activity may be determined by a trs endonuclease assay (see, e.g., Im et al., (1992) *J. Virology* 66:1119). Illustrative techniques for assaying other Rep functions are described in more details in the Examples section.

The ts phenotype may be ascertained with Rep proteins that are expressed outside of the wild-type context (e.g., the Rep proteins produced by the pHIV-Rep, pStump68, or pHIV-78 constructs described herein) or within the context of all four Rep proteins (e.g., from the pIM45 plasmid described herein). Preferably, the ts AAV Rep proteins exhibit a ts phenotype in both model systems.

In exemplary embodiments, the ts Rep protein is heat sensitive and exhibits at least about a 50% reduction in at least one Rep function at about 37° C. as compared with the wild-type Rep protein. In another illustrative embodiment, a heat sensitive ts Rep protein demonstrates at least about a 75% reduction in at least one Rep protein activity at about 39° C. as compared with the wild-type Rep protein. In a further illustrative embodiment, the ts Rep protein is heat sensitive and exhibits at least about a 50% reduction in at least one Rep function at 37° C. as compared with the activity of the ts Rep protein at permissive temperatures (e.g., 32° C.). In yet another embodiment, a heat sensitive ts Rep protein demonstrates at least about a 75% reduction in at least one Rep protein activity at about 39° C. as compared with the activity of the ts Rep protein at permissive temperatures (e.g., 32° C.).

The primary amino acid sequence of the AAV Rep proteins is fairly conserved (Chiorini et al., (1999) *J. Virology* 73:1309). The amino terminal portions of the Rep78 and Rep68 proteins have been associated with DNA binding and replication activities. The ts Rep proteins of the present invention are preferably Rep78 or Rep68 proteins comprising one or more mutations in the amino terminal half of thereof, more preferably the amino terminal 260 amino acids, which confer a ts phenotype for at least one Rep protein function. Also preferred are ts Rep78 and ts Rep68 proteins with one or more mutations in the regions defined by amino acids 25–75, 76–124, or 125–260.

In particular preferred embodiments, the ts AAV Rep proteins are Rep78 or Rep68 proteins with a mutation at amino acid position 40, 42 and/or 44 of the AAV Type 1–Type 6 proteins, or the corresponding positions of other AAV Rep proteins, as are known by those skilled in the art (see, e.g. Chiorini et al., (1999) *J. Virology* 73:1309, which is incorporated herein in its entirety by reference), wherein the mutation(s) confers a ts phenotype on the protein, as described herein. More preferably, the AAV Rep78 or Rep68 protein has two or more mutations at amino acid positions 40, 42 and/or 44, most preferably at all three positions.

The term "mutation" as used herein may be any mutation known in the art, including but not limited to, insertion, deletion and missense mutations, but is preferably a missense mutation. The missense mutation(s) may result in any amino acid substitution(s) that confers a ts Rep phenotype.

The term "amino acid" as used herein refers to natural amino acids, non-naturally occurring amino acids, and amino acid analogs, all in their D and L stereoisomers. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y) and valine (V). Non-naturally occurring amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

Amino acid analogs include the natural and non-naturally occurring amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

Particularly preferred missense mutations are those that result in the substitution of an uncharged amino acid residue for a charged residue, as is known in the art (A. L. Lehninger, Principles of Biochemistry, Worth Publishers, Inc., (1982), Chapt. 5). More preferably the mutation results in a small, non-polar amino acid residue (e.g., not an aromatic amino acid), other than proline (Id.). While not wishing to be held to any theory of the invention, it is believed that charged residues are primarily found on the surface of the molecule and are therefore less essential for protein folding and stability. However, the effects of substitution may be exacerbated at elevated (or conversely, lowered) temperatures, resulting in a ts phenotype.

In particular preferred embodiments, the missense mutation(s) results in the substitution of an alanine, glycine, isoleucine, leucine, valine, beta-alanine, allo-isoleucine, N-methylglycine, N-methylisoleucine, N-methylvaline, norvaline, or norleucine residue(s) for the charged amino acid(s) found in the wild-type protein. Most preferably, the missense mutation(s) results in the substitution of an alanine residue(s).

In particular illustrative embodiments described herein are ts AAV Rep78 and Rep68 proteins with missense mutations to substitute an alanine at amino acid positions 40, 42 and 44 (of the AAV Types1–6 Rep proteins, or the corresponding amino acids of other AAV proteins, as is known by those skilled in the art, see, e.g., Chiorini et al., (1999) *J. Virology* 73:1309; international patent publication WO 00/28061 to Wilson et al.). For AAV serotypes 1–4 and 6, the missense mutations result in aspartic acid to alanine (D→A) substitutions at all three positions. For AAV serotype 5, the mutations are E40, D42, N44→A at all three positions.

Davis et al., (1999) *J. Virology* 73:2084, have described an AAV Rep68-maltose binding protein (MBP) fusion with D→A substitutions at amino acids 40, 42 and 44. The MBP was expressed at the amino terminus of the Rep68 mutant, and was employed to facilitate purification of the Rep68 protein by amylose affinity chromatography.

Davis et al. observed a non-conditional Rep phenotype for binding and trs endonuclease activity with the Rep-68(D40, 42,44A)-MBP protein. These investigators reported that the Rep-68(D40,42,44A)-MBP exhibited no DNA binding activity to AAV hairpin DNA or trs endonuclease activity (although they did observe helicase activity, ATPase activity, and Rep-Rep interactions with this mutant in vitro). From these studies, it appears likely that fusion of the large MBP to the amino-terminus of Rep68 perturbed the function of the Rep68 protein, even in the wild type form, so that the effects of particular mutations could not be evaluated independently of the MBP moiety. To illustrate this point, Davis et al. employed 500-fold more of the wild-type Rep68 in their DNA binding studies than were used in the investigations described in the Examples section below. Thus, the MBP modification dramatically impaired the function of the wild type Rep68 protein, making it an unsuitable template for assessing the effects of other mutations on Rep function.

According to the present invention, the ts Rep protein may contain modifications, such as a histidine tag to assist in purification. However, it is preferred that the protein is not modified by fusion (or other covalent attachment to) a bulky molecule such as the maltose binding protein of Davis et al. It is further preferred that modifications to the protein are avoided that would substantially interfere with the activity of the Rep protein at permissive temperatures.

In contrast to the MBP fusion protein of Davis et al., the inventive ts AAV Rep proteins disclosed herein exhibit Rep activity (as described above) at permissive temperatures (e.g., 32° C.). In particular, the AAV Rep proteins of the present invention exhibit DNA binding, DNA replication, viral replication, and/or site- and strand-specific endonuclease activity at permissive temperatures. Preferably, at permissive temperatures, the ts AAV Rep proteins of the invention have at least about 33%, 50%, 75%, 90% or more of the activity of the wild-type Rep protein evaluated under similar conditions, although as described above, this activity may be delayed as compared with wild-type activity.

Urabe et al., (1999) *J. Virology* 73:2682, performed charge to alanine mutagenesis in the context of an AAV Rep78 protein that also included a G→E substitution at amino acid position 17 (in the DNA binding domain) and a M→G mutation at amino acid 225. Additional (individual) D→A mutations were made at amino acid positions 40, 42 or 44 (also in the DNA binding domain). All three mutants exhibited DNA binding and nicking activities similar to the wild-type protein. In contrast, the D42A mutant showed weak to no site-specific integration activity, whereas the D40A and D44A mutants demonstrated wild-type integration activity. These investigators did not report a ts Rep phenotype for any of these mutants.

As a further preferred embodiment, the ts Rep proteins of the present invention may additionally contain one or more mutations that render the protein relatively unstable or labile (i.e., more rapid half-life or turnover) as compared with the Rep protein in the absence of the mutation. The destabilizing mutation may be any mutation known in the art (e.g., insertion, deletion or missense). In particularly preferred embodiments, the mutation is at the p19 start site for the smaller Rep proteins and/or the 5' splice-site donor site in the rep coding sequences. It is preferable, but not necessary, that these mutations reduce or even ablate the activity of these sites.

It is further preferred that these mutations increase the turnover rate of the ts Rep protein at non-permissive temperatures. In this way, these mutations may be incorporated into a ts Rep protein to advantageously provide an additional control mechanism. The activity of the ts Rep may be modulated by shifting to a non-permissive temperature. The destabilizing mutations will provide a further safeguard to prevent cytopathic effects or other toxic activity normally associated with Rep proteins. The p19 start site and 5' splice site destabilizing mutations may further by used with any AAV Rep protein (e.g., a wild type or other non-ts Rep protein) to advantageously increase Rep protein turnover.

In particular preferred embodiments, the p19 mutation is a missense mutation at nt 993–994 of the AAV type 2 genome (or the corresponding nucleotides in other AAV, as is known by those skilled in the art; see, e.g., Chiorini et al., (1999) J. Virology 73:1309; international patent publication WO 00/28061 to Wilson et al.; e.g., nt 1007–1008 for AAV1, nt 990–991 for AAV3, nt 1044–1045 for AAV4, nt 1019–1020for AAV5, nt992–993 for AAV6). These missense mutations give rise to an amino acid substitution at the p19 start site; preferably, this mutation results in a M to G change in the protein. In AAV1, AAV2, AAV3, AAV4 and AAV6 this results in a substitution at amino acid position 225 of Rep78 or Rep68. In AAV6, this missense mutation results in a substitution at amino acid position 221 of Rep78/68.

In other preferred embodiments, the 5' splice donor site mutation is at nt 1907–1908 of the AAV type 2 genome (or the corresponding nucleotides in other AAV, as is known by those skilled in the art; see, e.g., Chiorini et al., (1999) J. Virology 73:1309; international patent publication WO 00/28061 to Wilson et al.; e.g., nt 1924–1925 of AAV1, nt 1904–1905 of AAV3, nt 1958–1959 of AAV4; nt 1929–1930 of AAV5; nt 1909–1910 of AAV6). These missense mutations give rise to amino acid substitutions in the protein at the 5' splice donor site; preferably, this mutation results gives rise to a RY to SN change in the protein. In AAV2, AAV3 and AAV4, this missense mutation results in a substitution at amino acid positions 529 and 530 (using Rep78 numbering). In AAV1, AAV5 and AAV6, this missense mutation gives rise to a substitution at amino acids 530–531, 544–545 or 530–531, respectively (using Rep78 numbering).

In a particular illustrative embodiment, the ts Rep protein is a ts Rep78 incorporating both the p19 start site and splice site mutations. Another exemplary preferred embodiment is a ts Rep68 protein comprising the mutation at the p19 promoter.

The ts AAV Rep proteins of the invention can be used in accordance with any of the methods described hereinbelow for producing or administering AAV vectors. The ts AAV Rep proteins are further suitable for in vitro packaging methods; by shifting the reaction mixture to a non-permissive temperature, Re protein can be reduced or eliminated so that packaging of template does not compete with replication. Alternatively, the inventive ts AAV Rep proteins find use in methods of mapping antigenic regions of the AAV Rep proteins, studying activity/function relationships of the AAV Rep proteins, and/or for producing antibodies against the novel AAV Rep protein structures.

Nucleotide Sequences, Vectors, and Cells of the Invention

The present invention also provides isolated nucleotide sequences encoding the ts AAV Rep proteins described hereinabove. The inventive nucleotide sequences can be single or double-stranded DNA, RNA or DNA-RNA hybrid sequences (including both naturally occurring and non-naturally occurring nucleotides), but are preferably either single or double stranded DNA sequences.

The nucleotide sequence may encode one, two, three or all four of the AAV Rep proteins. In those embodiments in which the nucleotide sequence encodes one or more ts AAV Rep proteins, it is not necessary that all of the Rep proteins encoded by the nucleotide sequence have a ts phenotype. One, two, three or all four of the Rep proteins may be ts (as that term is described above). Preferably, the nucleotide sequence encodes a ts Rep78 and/or a ts Rep68 protein. In particular embodiments, the nucleotide sequence further encodes a wild-type or ts Rep52 and/or a wild-type or ts Rep40 protein. In illustrative preferred embodiments, the nucleotide sequence encodes (a) a ts Rep78 protein, or (b) a ts Rep78 protein and a ts Rep68 protein, or (c) a ts Rep78, ts Rep68, Rep52 and Rep40 proteins. As a further alternative, the nucleotide sequence may encode two or more copies of one or all of the AAV Rep proteins.

The sequences encoding the ts Rep protein may be outside of the wild-type context (e.g., the pHIV-Rep, pStump68, or pHIV-78 constructs described herein) or within the context of the rep genes encoding all four Rep proteins (e.g., the pIM45 plasmid described herein).

The ts AAV Rep proteins encoded by the inventive nucleotide sequences are as described above. Preferably, the one or more nucleotide sequence contains a missense mutation(s) that results in amino acid substitutions as compared with the wild type sequence, which mutation(s) confer the ts phenotype. More preferably, the nucleotide sequence encodes a missense mutation at amino acid positions 40, 42 and/or 44 (of the AAV Type 1 to Type 6 proteins, or the corresponding positions of the proteins from other AAV, as is known by those skilled in the art) that produces a ts AAV Rep78 protein and/or a ts Rep68 protein (as described above). In still further preferred embodiments, the nucleotide sequence encodes a Rep78 or Rep68 protein with missense mutations at amino acid positions 40, 42 and 44.

In particularly preferred embodiments, the missense mutations at amino acid 40, 42 and 44 result from an A to C mutation at nucleotides 439, 445, and 451, respectively, of the AAV type 2 genome (or the corresponding position of the genomes of other AAV, see, e.g., Chiorini et al., (1999) J. Virology 73:1309; international patent publication WO 00/28061 to Wilson et al.; nt 453, 459 and 465 of AAV1, nt 436, 442, and 448 of AAV3, nt 490, 496 and 502 of AAV4, nt 477, 483 and 489 of AAV5, and nt 438, 444 and 450 of AAV6).

The nucleotide sequence encoding the ts Rep protein(s) may optionally encode other mutations and/or modifications to the Rep protein in addition to the mutation conferring a ts phenotype, as was detailed above in connection with the description of the ts AAV Rep proteins of the invention. In addition, those skilled in the art will understand that due to the overlapping coding regions of the AAV Rep proteins, a particular mutation(s) may affect more than one, or even all, of the encoded Rep proteins.

The nucleotide sequence encoding the ts AAV Rep protein (s) may be operably associated with any suitable expression control element, e.g., a promoter and/or enhancer element. The choice of promoter/enhancer may be influenced by the desired level and specificity of expression, the use of the nucleotide sequence (e.g., vector production versus gene delivery), and other factors appreciated by those skilled in the art. The promoter/enhancer element may be constitutive or inducible, depending on the pattern of expression desired. The promoter/enhancer element may be native (i.e., the AAV p5 and p19 promoters) or foreign and can be a natural or a synthetic sequence. The p5 promoter may also be advantageously employed to provide normal regulation of Rep expression, including induction by the adenovirus early gene products and/or Rep feedback inhibition.

Inducible expression control elements are preferred in those applications in which it is desirable to provide another level of control over expression of Rep activity (in addition to temperature regulation). Inducible promoters/enhancer elements for gene delivery are preferably tissue-specific promoter/enhancer elements, and include muscle specific (including cardiac, skeletal and/or smooth muscle), neural tissue specific (including brain-specific), liver specific, bone marrow specific, pancreatic specific, spleen specific, retinal specific, and lung specific promoter/enhancer elements. Other inducible promoter/enhancer elements include hormone-inducible (e.g., MMTV long terminal repeat) and metal-inducible elements. Exemplary inducible promoters/enhancer elements include but are not limited to a heat shock promoters, Tet on/off elements (e.g., promoters derived the E. coli TN10-specific tetracycline resistance operon), promoters derived from the lac repressor operator inductor system, RU486-inducible promoters, ecdysone-inducible promoters, rapamycin-inducible promoters, and metalothionein promoters.

The inventive nucleotide sequences may further include other AAV elements, such as the AAV cap genes and/or one or more AAV inverted terminal repeats (ITRs). Typically, the sequences encoding AAV Rep and Cap proteins will not be flanked by the ITRs to prevent packaging of these sequences. Moreover, the nucleotide sequence may contain one or more heterologous (i.e., foreign) nucleotide sequences of interest (e.g., two, three or more heterologous nucleotide sequences), typically operably associated with one or more AAV ITRs.

In particular preferred embodiments, the nucleotide sequence encodes a ts Rep protein(s) and further encodes an AAV template, e.g., to be packaged or delivered to a cell. Typically, and preferably, the sequences encoding the ts Rep protein are outside of the AAV ITRs. It is further preferred that the AAV template comprises one or more heterologous nucleotide sequences flanked by 5' and 3' ITRs.

The rAAV template may encode at least one AAV inverted terminal repeat, preferably two AAV inverted terminal repeats, which flank the 5' and 3' ends of the heterologous nucleic acid sequence(s) to be delivered to a target cell. The term "inverted terminal repeat" includes synthetic sequences, such as the "double-D sequence" as described in U.S. Pat. No. 5,478,745 to Samulski et al., the disclosure of which is incorporated in its entirety herein by reference. It has been demonstrated that only a single 165 bp double-D sequence is required in cis for site specific integration, replication, and encapsidation of vector sequences.

Heterologous nucleotide sequences of interest include nucleotide sequences encoding peptides and proteins, preferably therapeutic (e.g., for medical or veterinary uses) or immunogenic peptides or proteins (e.g., for an immunogenic composition).

A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject. Therapeutic peptides and proteins include, but are not limited to, CFTR (cystic fibrosis transmembrane regulator protein), dystrophin (including the protein product of dystrophin mini-genes, see, e.g, Vincent et al., (1993) Nature Genetics 5:130), utrophin (Tinsley et al., (1996) Nature 384:349), clotting factors (Factor XIII, Factor IX, Factor X, etc.), erythropoietin, the LDL receptor, lipoprotein lipase, ornithine transcarbamylase, $\beta$-globin, $\alpha$-globin, spectrin, $\alpha$-antitrypsin, adenosine deaminase, hypoxanthine guanine phosphoribosyl transferase, $\beta$-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor -3 and -4, brain-derived neurotrophic factor, glial derived growth factor, transforming growth factor-$\alpha$ and -$\beta$, and the like), cytokines (e.g., $\alpha$-interferon, $\beta$-interferon, $\gamma$-interferon, $\omega$-interferon, $\tau$-interferon, interleukin-1$\alpha$, interleukin-1$\beta$, interleukin-2, interleukin-3, interleukin-4, interleukin 5, interleukin-6, interleukin-7, interleukin-8, interleukin-9, interleukin-10, interleukin-10, interleukin-11, interleukin 12, interleukin-13, interleukin-14, interleukin-18, B cell Growth factor, CD40 Ligand, tumor necrosis factor-$\alpha$, tumor necrosis factor-$\beta$, monocyte chemoattractant protein-1, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may used in the treatment of a disease condition including, but not limited to, cystic fibrosis (and other diseases of the lung), hemophilia A, hemophilia B, thalassemia, sick cell anemia and other blood disorders, AIDS, amyloid polyneuropathy, Alzheimer's disease, Parkinson's disease, Huntington's disease, amylotrophic lateral sclerosis, epilepsy, and other neurological disorders, cancer, diabetes mellitus, muscular dystrophies (e.g., Duchenne, Becker), Gaucher's disease, Hurler's disease, Lesch-Nyhan syndrome, adenosine deaminase deficiency, glycogen storage diseases and other metabolic defects, retinal degenerative diseases (and other diseases of the eye), and diseases of solid organs (e.g., brain, liver, kidney, heart).

As a further alternative, the heterologous nucleic acid sequence may encode a reporter peptide or protein (e.g., an enzyme). Reporter proteins are known in the art and include, but are not limited to, Green Fluorescent Protein, $\beta$-galactosidase, alkaline phosphatase, chloramphenicol acetyltransferase, and the like.

Alternatively, in particular embodiments of the invention, the nucleic acid of interest may encode an antisense nucleic acid, a ribozyme (e.g., as described in U.S. Pat. No. 5,877,022), RNAs that effect spliceosome-mediated trans-splicing (Puttaraju et al., (1999) Nature Biotech. 17:246), or other non-translated RNAs, such as "guide" RNAs (Gorman et al., (1998) Proc. Nat. Acad. Sci. USA 95:4929; U.S. Pat. No. 5,869,248 to Yuan et al.), and the like.

The AAV vector may also encode a heterologous nucleotide sequence that shares homology with and recombines with a locus on the host chromosome. This approach may be utilized to correct a genetic defect in the host cell.

An immunogenic protein or peptide, or immunogen, may be any protein or peptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen, or any other vaccine antigen known in the art.

Alternatively, the immunogen may be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to: MART-1/ MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15, and p53 antigens.

It will be understood by those skilled in the art that the heterologous nucleotide sequence(s) of interest may be operably associated with appropriate transcription/ translation control signals and polyadenylation signals. In addition, a variety of promoter/enhancer elements may be used depending on the level and tissue-specific expression desired. The promoter/enhancer element can be constitutive or inducible, depending on the pattern of expression desired. The promoter/enhancer element may be native or foreign and can be a natural or a synthetic sequence. By foreign, it is intended that the transcriptional initiation region is not found in the wild-type host into which the transcriptional initiation region is introduced. Promoter/enhancer elements that are native to the target cell or subject to be treated are most preferred. Also preferred are promoters/enhancer elements that are native to the heterologous nucleic acid sequence. The promoter/enhancer element is chosen so that it will function in the target cell(s) of interest. Mammalian promoter/enhancer elements are also preferred. The promoter/enhance element may be constitutive or inducible (as this term is described in more detail above).

In embodiments of the invention in which the heterologous nucleotide sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

The present invention also encompasses vectors comprising the nucleotide sequences encoding the inventive ts AAV Rep protein(s) and/or the AAV template to be packaged or delivered. The vector may be any vector known in the art. Illustrative vectors include, but are not limited to, plasmids, naked DNA vectors, bacterial artificial chromosomes (BACs), yeast artificial chromosomes (YACs), cosmids, and viral vectors.

Any suitable viral vector may be employed, as known in the art, including, single and double-stranded RNA and DNA viral vectors, with DNA being preferred. Exemplary viral vectors may be derived be from Poxviridae (e.g., pox virus or vaccinia virus), Papoviridae (e.g., BKV, JCV, or SV40), Adenoviridae (e.g., adenovirus), Herpesviridae (e.g., Herpes Simplex Virus), Hepadnaviridae (e.g., HBV), Retroviridae (e.g., HIV, SIV, MoMLV, RSV, HTLV), Picornaviridae (e.g., poliovirus, rhinovirus, coxsackieviruses, Caliciviridae, Togaviridae (e.g., alphaviruses, rubella) Flaviviridae (e.g., yellow fever virus), Parvoviridae (e.g., AAV), Coronaviridae (e.g., HDV, TGEV, IBV, MHV, BCV), Rhabdoviridae, Filoviridae, Paramyxoviridae (e.g., parainfluenza virus, mumps virus, measles virus, and respiratory syncytial virus), Orthomyxoviridae (e.g., influenza virus), Bunyaviridae, Arenaviridae, hepatitis delta virus, Astroviruses, Epstein Barr Virus (EBV) and non-mammalian viruses, such as baculoviruses.

Preferred viral vectors include AAV, adenovirus, herpesvirus, EBV, baculovirus, and retroviral (e.g., lentiviral) vectors, more preferably, adenovirus and herpesvirus vectors.

Other preferred vectors are set forth below in connection with the description of gene delivery and vector production methods.

In particular and preferred embodiments, the present invention provides pStump68, pHIV-Rep, pHIV-78, and pIM45 derived vectors encoding proteins containing ts mutations (e.g., alanine substitutions) at amino acid positions 40, 42 and 44.

The present invention also encompasses cells containing the inventive nucleotide sequences, vectors and ts Rep proteins described above. The cell may be any cell known in the art, including bacterial, protozoan, yeast, fungal, plant and animal cells. Animal cells (e.g., insect and mammalian cells) are preferred. Mammalian cells are more preferred, with human cells being most preferred. In particular embodiments, the cell is a target cell for gene delivery, alternatively, the cell is a permissive cell for vector production.

Preferred target cells for packaging AAV or adenovirus vectors, or for ex vivo gene delivery, are as described in detail below.

Hybrid Adenovirus Vectors

It is currently not feasible to generate optimum cell lines for packaging AAV vectors due to toxicity of the AAV gene products (i.e., the Rep proteins) to the packaging cells. The AAV Rep proteins also appear to interfere with adenovirus replication. This phenomenon has hindered the creation of effective hybrid helper adenoviruses expressing the AAV rep genes. Thus, current protocols for AAV vector production require that the AAV rep/cap sequences and adenovirus helper functions be provided on separate constructs. These factors have been problematic for the development of scalable AAV vector production schemes.

As one example, Recchia et al., (1999) *Proc. Natl. Acad. Sci. USA* 96:2615, describe efforts to produce an adenovirus expressing an AAV Rep78 gene. This hybrid adenovirus was poorly replicated during serial passages in a packaging cell line; titers of only 50–100 transducing units/cell were achieved. In addition, this group was unable to isolate an Ad/AAV hybrid carrying all four Rep proteins due to toxicity.

These limitations may be reduced or overcome by the ts AAV Rep proteins of the present invention. Cytotoxicity and interference with helper virus function can be avoided at non-permissive temperatures for the ts Rep protein(s). The system may be activated by shifting to permissive temperatures to allow replication and packaging of the AAV vector.

Accordingly, the present invention provides a hybrid adenovirus vector stably comprising an AAV rep coding sequence, and adenoviruses containing the hybrid adenovirus vector. By "stably comprising an AAV rep coding sequence", it is intended that the sequences encoding the ts AAV Rep protein(s) are maintained by the adenovirus genome during serial replication cycles at non-permissive temperatures (e.g., at least about 2, 5, 10, 20, 100, 1000, 5000 or even more replication cycles). In other preferred embodiments, the hybrid adenovirus "stably" comprises the coding sequences for the ts AAV Rep protein for at least about 2, 5, 10, 20, 100, 1000 days, or even longer, at non-permissive temperatures.

In addition, according to the present invention, high-titer stocks of the hybrid adenovirus encoding the ts AAV Rep protein(s) may be produced at non-permissive temperatures (e.g., greater than about 100 infectious transducing units (tu)/cell, 500 tu/cell, 1000 tu/cell, 5000 tu/cell, 10,000 tu/cell, or more). Preferably, the hybrid adenovirus can be generated to essentially wild-type titers (e.g., at least about 90%, 95%, 99% or more of wild-type levels) at non-permissive temperatures.

The nucleotide sequences encoding the ts AAV Rep protein(s) are as detailed above. For the purposes of packaging AAV vectors, it is preferred that all four AAV Rep proteins are encoded by the hybrid adenovirus genome. Preferably, the Rep78 and/or Rep68 proteins have a ts phenotype. Also preferred are embodiments wherein all four of the Rep proteins have a ts phenotype. In the most preferred embodiments of the invention, the Rep78 and Rep68 proteins exhibit a ts phenotype. Typically, and preferably, if the hybrid adenovirus vector encodes a Rep78 or a Rep68 protein, it will be a ts mutant, as a non-ts form of one or both of the large Rep proteins will not readily be tolerated and maintained.

The hybrid adenovirus vector optionally, and preferably, also encodes the AAV Cap proteins. It is further preferred that the nucleotide sequences encoding the AAV Rep protein(s) are operably associated with inducible promoters, as described above. Alternatively, the rep coding sequences may be operatively associated with the AAV p5 promoter. It is preferred that the AAV rep/cap sequences cannot be packaged within an AAV particle (e.g., are not operatively associated with the AAV packaging sequences).

In other preferred embodiments, the hybrid adenovirus vector further comprises an AAV template embedded within the adenovirus backbone (i.e., between the adenovirus terminal repeats). Typically, the AAV template encodes one or more heterologous nucleotide sequences flanked by one or more AAV ITRs. Advantageously, according to this embodiment, the AAV vector may carry large heterologous nucleotide sequences that exceed the packaging limits of the AAV capsid. For example, if the rAAV is embedded within a gutted adenovirus, up to approximately 36 kb of sequence may be packaged.

Alternatively, or in addition, the hybrid adenovirus vector may comprise AAV replication and packaging sequences (i.e., the AAV rep and cap sequences) that are embedded within the adenovirus backbone. If the hybrid adenovirus contains both the rep/cap sequences and an AAV template, it is generally desirable to position the rep/cap sequences outside of the AAV ITRs, to prevent packaging thereof. rAAV vectors, heterologous nucleotide sequences, and the AAV ITRs are all as described in more detail above.

The adenovirus may further comprise the adenovirus sequences which provide helper functions essential for a productive AAV infection. In general, the helper functions are provided by the adenovirus early genes, more particularly, the E1a, E2a, E4orf6 and VA RNA adenovirus sequences.

Thus, the present invention provides an adenovirus helper that advantageously provides the AAV and adenovirus helper sequences for replication and packaging AAV particles in a single construct. The adenovirus will maintain the rep sequences if maintained at a non-permissive temperature for the ts Rep78 and/or ts Rep68. The AAV template may be further carried by this adenoviral vector (e.g., within the deleted E3 region), so that a single infection step may be used to provide all the components necessary to replicate and package a rAAV vector.

The adenovirus backbone will typically contain the 5' and 3' cis elements of the adenovirus genome for viral replication and packaging (i.e., the terminal repeats and the PAC sequence at the 5' end of the adenovirus genome). Thus, the hybrid adenoviral vector can be replicated and packaged as an adenovirus particle.

The adenovirus vector may be an E3 deleted adenovirus, which will alleviate the need to replicate the adenovirus on a trans-complementing packaging cell or in the presence of a helper virus providing the deleted function in trans.

In other embodiments, the hybrid adenovirus vector is a deleted adenovirus construct that results in a replication-defective virus. For example, first-generation adenovirus vectors are generally deleted for the E1 genes and packaged using a cell that expresses the E1 proteins (e.g., 293 cells). The E3 region is also frequently deleted as well, as there is no need for complementation of this deletion in vitro. In addition, deletions in the E4, E2a, DNA polymerase, pre-terminal protein, protein IX, and fiber protein regions have been described, e.g., by Hu et al., (1999) *Human Gene Therapy* 10:355; Amalfitano et al., (1998) *J. Virology* 72:926; Armentano et al, (1997) *J. Virology* 71:2408; Gao et al., (1996) *J. Virology* 70:8934; Dedieu et al., (1997) *J. Virology* 71:4626; Wang et al., (1997) *Gene Therapy* 4:393; U.S. Pat. No. 5,882,877 to Gregory et al. (the disclosures of which are incorporated herein in their entirety). Preferably, the deletions are selected to avoid toxicity to the packaging cell. Wang et al., (1997) *Gene Therapy* 4:393, has described toxicity from constitutive co-expression of the E4 and E1 genes by a packaging cell line. Toxicity may be avoided by regulating expression of the E1 and/or E4 gene products by an inducible, rather than a constitutive, promoter. Gutted adenoviruses with a theoretical packaging capacity of up to 35 kb of heterologous nucleotide sequences have also been described, and are most preferred (Kumar-Singh et al., (1996) *Human Molecular Genetics* 5:913).

Those skilled in the art will appreciate that deleted replication-defective adenoviruses may be propagated (e.g., to grow viral stocks) in the presence of a suitable helper virus or on a suitable packaging cell line, as known in the art and described below.

As a further non-limiting alternative, the hybrid adenovirus vector may have lox sites flanking the packaging sequence and the packaging cell produces the Cre recombinase protein. The presence of the Cre recombinase results in lox mediated recombination and removal of all sequences flanked by the lox sites (e.g., the packaging signal and/or other adenovirus sequences) and prevents the lox-containing DNA from being packaged (Parks et al., (1996) *Proc. Natl. Acad. Sci. USA* 93:13565). In a variation of this methodology the lox sites are placed within the multiply deleted vector flanking a greater amount of the Ad genome. When placed into Cre cells a large portion of the deleted vector genome is removed. The resulting reduced helper virus is purified away from the unloxed vector via cesium chloride centrifugation or other methods known in the art (Lieber et al., (1996) *J. Virol.* 70:8944; Kochanek et al., (1996) *Proc. Natl. Acad. Sci. USA* 93:5731).

The total size of the hybrid adenovirus is approximately 36 kb, preferably ranging from about 29 kb to about 37 kb in size. Accordingly, heterologous nucleotide sequences that exceed the capacity of the AAV capsid may be delivered cell according to the inventive methods disclosed herein. In a gutted adenovirus system, heterologous sequences approaching 35–36 kb may theoretically be packaged.

Herpesvirus may also be used as a helper virus in AAV packaging methods. Hybrid herpesviruses encoding the inventive ts AAV Rep protein(s) would also be desirable for more scalable AAV vector production schemes. A hybrid herpes simples virus type I (HSV-1) vector expressing the AAV-2 rep and cap genes has been described (Conway et al., (1999) *Gene Therapy* 6:986 and WO 00/17377, the disclosures of which are incorporated herein in their entireties). The herpesvirus helper sequences required for a productive AAV infection have been identified as UL5, UL8, UL52 and UL29. Further preferred are deleted, or otherwise replication-defective, herpesviruses (i.e., amplicons).

Other possible hybrid viruses that may further provide helper functions for a productive AAV infection include EBV, cytomegalovirus and vaccinia viruses.

Temperature-Sensitive Regulation of AAV Vector Production

As a still further aspect, the present invention provides methods of producing AAV vectors using the inventive ts Rep proteins, particularly in conjunction with the above-described hybrid adenovirus and herpesvirus vectors.

In one particular embodiment, the present invention provides a method of producing an infectious rAAV particle, comprising providing to a cell, (a) a rAAV template comprising (i) one or more heterologous nucleotide sequences, and (ii) AAV packaging signal sequences sufficient for the encapsidation of the AAV template into infectious rAAV particles, and (b) AAV sequences sufficient for replication and packaging the AAV template into infectious viral particles (e.g., the AAV rep and cap sequences), wherein the AAV sequences encode a ts AAV Rep protein, and further wherein the AAV Rep protein is a ts Rep78 and/or ts Rep68 protein. The rAAV template and AAV replication and packaging sequences are provided under conditions permissive for the ts AAV Rep protein(s), so that infectious rAAV particles comprising the rAAV template are produced in the cell. The method may further comprise the step of collecting the infectious rAAV particles from the cell. Infectious virus particles may be collected from the medium and/or by lysing the cells.

The cell is typically a cell that is permissive for AAV viral replication. Any suitable cell known in the art may be employed. Mammalian cells are preferred. Also preferred are trans-complementing packaging cell lines that will provide functions deleted from a replication-defective helper virus, e.g., 293 cells or other E1a trans-complementing cells.

The rAAV template comprises "AAV packaging signal sequences sufficient for the encapsidation of the AAV template into infectious rAAV particles" as known in the art. For example, the rAAV template may contain one or more AAV ITR sequences. Preferably, the rAAV template comprises two AAV ITRs that flank the 5' and 3' ends of the heterologous nucleotide sequence(s). The packaging sequences may further be modified or truncated AAV ITR sequences, or synthetic sequences, as described in more detail above.

The rAAV template and the AAV replication and packaging sequences are provided under conditions permissive for the ts AAV Rep protein(s). This phrase is intended to be broadly construed and does not necessarily mean that the cell is already at a permissive temperature at the time the rAAV template and AAV replication/packaging sequences are supplied. For example, these reagents may be provided to a cell at a non-permissive temperature, and then the cell may be shifted to a permissive temperature for the ts Rep protein. The cell may be further shifted back to a non-permissive temperature, e.g., to give a burst of Rep activity, or even cycled between permissive and non-permissive temperatures.

The rep coding sequences encoding the ts Rep protein(s) are as described above. For packaging rAAV particles, it is preferred that all four of the AAV Rep proteins are provided. Preferably, both the Rep78 and Rep68 proteins are ts as described herein.

The AAV replication and packaging sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector, as described in detail above. For example, the rep/cap sequences may be provided by a hybrid adenovirus or herpesvirus vector, as described in the previous section (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome", see Margolski, (1992) *Curr. Top. Microbiol. Immun.* 158:67).

As a further alternative, the rep/cap sequences may be stably embedded within a cell.

Typically, and preferably, the AAV rep/cap sequences will not be flanked by the AAV packaging sequences (e.g., AAV ITRs), to prevent rescue and/or packaging of these sequences.

The rAAV template is as described hereinabove, and may be provided to the cell using any method known in the art. For example, the rAAV template may be supplied by a non-viral (e.g., plasmid) or viral vector (as described above). In particular preferred embodiments, the rAAV template is supplied by a herpesvirus or adenovirus vector (e.g., inserted into the E1a or E3 regions of a deleted adenovirus). As another illustration, Palombo et al., (1998) *J. Virology* 72:5025, describe a baculovirus vector carrying a reporter gene flanked by the AAV ITRs. EBV vectors may also be employed to deliver the rAAV template, as described above with respect to the rep/cap genes.

In another preferred embodiment, the AAV template is provided by a replicating rAAV virus. In still other embodiments, an AAV provirus is stably integrated into the chromosome of the cell.

To obtain maximal rAAV titers, helper virus functions (e.g., adenovirus or herpesvirus) essential for a productive AAV infection will be provided to the cell. Helper virus sequences necessary for AAV replication are known in the art and are described hereinabove. Typically, these sequences will be provided by a helper adenovirus or herpesvirus (preferably, adenovirus) vector. Alternatively, the adenovirus or herpesvirus sequences may be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes embedded in the chromosome or maintained as a stable extrachromosomal element. It is preferred that these helper virus sequences cannot be packaged into AAV virions, e.g., are not flanked by AAV ITRs.

Those skilled in the art will appreciate that it may be advantageous to provide the AAV replication and packaging sequences and the helper virus sequences (e.g., adenovirus sequences) on a single helper construct. This helper construct may be a non-viral or viral construct, but is preferably a hybrid adenovirus or hybrid herpesvirus comprising the AAV rep/cap genes as described above.

In one particular preferred embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further preferred embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particles or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, it is preferred that the adenovirus helper sequences and the AAV rep/cap sequences are not flanked by the AAV packaging sequences (e.g., the AAV ITRs), so that these sequences are not packaged into the AAV virions.

Generally, the adenovirus is grown up at the non-permissive temperature for a time sufficient to produce an adenovirus stock, optionally in the presence of a suitable helper virus or in a suitable packaging cell as known in the art (i.e., to complement any genes deleted or inactivated in the adenovirus vector).

The adenovirus stock may then be used to infect a suitable cell permissive for AAV replication and packaging, preferably, at the permissive temperature for the ts Rep protein(s). Alternatively, the cell may be infected at a non-permissive temperature, and then shifted to a permissive temperature to induce Rep function. For example, the cell may be infected with the adenovirus at a low MOI, which is allowed to replicate at a non-permissive temperature. The cells may then be shifted to a permissive temperature for the ts Rep protein(s) to induce rAAV template replication and packaging.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of rAAV vector particles. Preferably, the AAV stock has a titer of at least about $10^5$ transducing units (tu)/ml, more preferably at least about $10^6$ tu/ml, more preferably at least about $10^7$ tu/ml, yet more preferably at least about $10^8$ tu/ml, yet more preferably at least about $10^9$ tu/ml, still yet more preferably at least about $10^{10}$ tu/ml.

Gene Transfer Technology

The methods of the present invention also provide a means for delivering heterologous nucleotide sequences into a broad range of cells, including dividing and non-dividing cells. The present invention may be employed to deliver a nucleotide sequence of interest to a cell in vitro, e.g., to produce a peptide or protein in vitro or for ex vivo gene therapy. The cells, pharmaceutical formulations, and methods of the present invention are additionally useful in a method of delivering a nucleotide sequence to a subject in need thereof, e.g., to express an immunogenic or therapeutic peptide or protein. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

In general, the present invention can be employed to deliver any heterologous nucleic acid to a cell, as described above.

One particular advantage of AAV vectors is that nucleotide sequences flanked by the ITRs are integrated into the genome of humans and simians at specific target sites. For example, the predominant integration site for AAV in the human genome is at chromosome 19q13-qter (Samulski et al., (1991) *EMBO J.* 10:3941, published erratum appear at *EMBO J.* (1992) 11:1228). Accordingly, the present invention may be employed for targeted integration of AAV vectors into human and simian chromosomes, as well as animal models containing the targeting locus (see, e.g., Rizzuto et al., (1999) *J. Virology* 73:2517).

Specific integration of AAV vectors into the genome may greatly reduce concerns regarding position effects and chromosome rearrangements and/or disruptions when developing gene delivery strategies. Most AAV vectors, however, replace all of the viral genome with the exception of the ITRs with one or more heterologous nucleotide sequences to be delivered by the vector. In the absence of Rep function, the vector randomly integrates throughout the genome. It is theoretically possible to co-transduce a second vector carrying the AAV rep genes. This approach raises clinical and regulatory concerns regarding viral replication in the host subject. Moreover, the Rep proteins are generally cytotoxic to host cells.

The ts AAV Rep proteins of the present invention offer a more reliable means of controlling Rep activity for targeted integration of AAV vectors into host cells. According to one embodiment, the inventive ts AAV Rep protein(s) and a rAAV vector are provided to a host cell. The rAAV vector comprises one or more heterologous nucleotide sequences to be delivered to the host cell flanked by one or more AAV ITRs. The host cell is maintained at a permissive temperature (e.g., 32° C.) and under conditions sufficient for the ts Rep protein to mediate targeted integration of the rAAV vector into the genome. The host cell may then be shifted to a non-permissive temperature to inactivate the ts AAV Rep protein. Alternatively, the ts AAV Rep protein is exposed to non-permissive temperatures upon administration to the subject.

It has been found that Rep78 and/or Rep68 are sufficient for integration. Thus, it is not required that all four AAV Rep proteins be provided to the host cell to achieve integration. Indeed, it appears that Rep52 and Rep40 may reduce the incidence of integration at the targeting locus. Accordingly, in preferred embodiments of the invention, a ts AAV Rep78 and/or ts Rep68 protein is provided. In those embodiments wherein both the Rep78 and Rep68 proteins are provided, it is further preferred that both proteins exhibit the ts phenotype.

The ts AAV Rep protein(s) may be provided to the host cell by any means known in the art. It is preferred, however, that the Rep protein(s) be provided in a non-integrating form (e.g. not flanked by AAV ITRs). The ts AAV Rep proteins may be encoded by any DNA template, as described herein. For example, the Rep protein functions may be provided in trans by a plasmid that is co-transfected with the vector carrying the rAAV genome. As a further alternative, the ts Rep protein(s) may be provided by a viral vector, preferably, a non-integrating viral vector, such as AAV, EBV, adenovirus, herpesvirus, or baculovirus.

As a further alternative, the ts AAV Rep protein(s) may be provided to the host cell by introducing mRNA encoding the ts Rep protein(s) into the cell by any means known in the art. As still a further alternative, the protein itself may be introduced, e.g., on the surface of a virus capsid, encapsulated in lipid, by microparticle bombardment, and the like. AAV Rep proteins may also be delivered into a cell using a "nonclassical" import/export signal peptide (e.g., fibroblast growth factor-1 and -2, interleukin 1, HIV-1 Tat protein, herpes virus VP22 protein, and the like) as described by Cleves, (1997) *Current Biology* 7:R318. The AAV Rep proteins may also be tagged with peptide motifs that direct uptake by specific cells, as is known in the art, e.g., a FVFLP peptide motif triggers uptake by liver cells.

The nucleotide sequences encoding the ts AAV Rep protein(s) described above may be operably associated with an expression control element(s) (e.g., a promoter/enhancer element). More preferably, the nucleotide sequence encoding the ts AAV Rep protein(s) is operably associated with an inducible promoter/enhancer element (as described above) so as to provide another level of regulation to expression of the Rep protein(s).

The ts Rep protein may further comprise a destabilizing mutation as described above (e.g., at the p19 start site or the 5' splice site).

The rAAV may also be provided by any method known in the art, as described hereinabove. The template may be delivered by any vector known in the art, including but not limited to, plasmids, BACs, YACs, naked DNA and viral vectors. Preferably, the rAAV template is delivered using a lipid encapsulated DNA vector, a plasmid, or a non-integrating viral vector (e.g., adenovirus, herpesvirus, baculovirus, or EBV). The rAAV template may further be provided by a rAAV virion. One advantage of providing the rAAV template outside the context of an infectious AAV particle is that other vectors may permit the packaging of large nucleotide sequences, greatly exceeding the size limitations of the AAV capsid, between the AAV ITRs.

In a more preferred embodiment of the invention, both the rAAV vector and the ts AAV Rep protein(s) are provided by a single non-viral or viral vector (as described in the preceding paragraph). This strategy is advantageous in that it requires a single transduction step. The tsRep protein acts in cis to mediate the integration of the rAAV vector into the host cell genome. The sequences encoding the Rep protein (s), however, would preferably not be integrated (i.e., use a non-integrating vector and the rep sequences are not flanked with ITRs).

Vectors encoding the rAAV genome or Rep protein(s) may be administered to the host cell by standard methods for ex vivo gene delivery, as are known in the art. For example, standard viral infection, liposome delivery, microparticle bombardment, electroporation, microinjection, and the like, may be employed using methods known in the art. The amount of vector provided to the host cell will depend upon the target cell type and the particular vector, and may be determined by those of skill in the art without undue experimentation.

The cell to be administered the inventive AAV vectors can be of any type, including but not limited to bone cells (including bone marrow progenitor cells), neural cells (including cells of the peripheral and central nervous systems, in particular, brain cells), retinal cells, lung cells, epithelial cells (e.g., gut and respiratory), muscle cells, pancreatic cells (including islet cells), hepatic cells, myocardial cells, spleen cells, keratinocytes, fibroblasts, endothelial cells, dendritic cells, germ cells, and the like. Alternatively, the cell may be any progenitor cell. As a further alternative, the cell can be a stem cell (e.g., neural stem cell, hematopoietic stem cell, liver stem cell). Moreover, the cells can be from any species of origin, as indicated above.

In particular embodiments of the invention, after the rAAV vector has been integrated into the cell, the cell is administered to a subject. For example, methods of ex vivo gene therapy are known wherein cells are removed from a subject, the rAAV vector is introduced therein, and the cells are then replaced back into the subject. Methods of removing cells from a subject for treatment ex vivo, followed by introduction back into the subject are known in the art. Alternatively, the rAAV vector is introduced into cells from another subject, into cultured cells, or into cells from any other suitable source, and the cells are administered to a subject in need thereof.

The cells transduced with the rAAV vector are preferably administered to the subject in a "therapeutically-effective amount" in combination with a pharmaceutical carrier. A "therapeutically-effective" amount as used herein is an amount that provides sufficient expression of the heterologous nucleotide sequence delivered by the rAAV vector to provide some improvement or benefit to the subject. Alternatively stated, a "therapeutically-effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In alternate embodiments, cells that have been transduced with the rAAV vector may be administered to elicit an immunogenic response against the delivered peptide or protein. Typically, a quantity of cells expressing an immunogenic amount of the peptide or protein in combination with a pharmaceutically-acceptable carrier is administered. An "immunogenic amount" is an amount of the expressed peptide or protein that is sufficient to evoke an active immune response in the subject to which the pharmaceutical formulation is administered. The degree of protection conferred by the active immune response need not be complete or permanent, as long as the benefits of administering the immunogenic peptide or protein outweigh any disadvantages thereof.

Subjects, Pharmaceutical Formulations, Vaccines, and Modes of Administration

The present invention finds use in both veterinary and medical applications. Suitable subjects for ex vivo gene delivery methods as described above include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are most preferred. Human subjects include neonates, infants, juveniles, and adults.

In particular embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc. For injection, the carrier will typically be a liquid, such as sterile, pyrogen-free water or sterile pyrogen-free phosphate-buffered saline solution. As an injection medium, it is preferred to use water that contains the additives usual for injection solutions, such as stabilizing agents, salts or saline, and/or buffers.

In alternate embodiments, the present invention provides a pharmaceutical formulation comprising a vector encoding a ts AAV Rep78 and/or ts AAV Rep68 protein, as described hereinabove. More preferably, the pharmaceutical formulation contains an adenovirus vector encoding a ts AAV Rep78 and/or ts AAV Rep68 protein, also as described hereinabove.

Also provided herein is a pharmaceutical formulation comprising a ts AAV Rep protein in a pharmaceutically-acceptable carrier. Preferably, the ts Rep is a ts Rep78 or a tsRep68 protein. More preferably, the pharmaceutical composition contains both a ts Rep78 and ts Rep68 proteins.

In general, a "physiologically acceptable carrier" is one that is not toxic or unduly detrimental to cells. Exemplary physiologically acceptable carriers include sterile, pyrogen-free water and sterile, pyrogen-free, phosphate buffered saline. Physiologically-acceptable carriers include pharmaceutically-acceptable carriers.

By "pharmaceutically acceptable" it is meant a material that is not biologically or otherwise undesirable, i.e., the material may be administered to a subject without causing any undesirable biological effects.

A pharmaceutical formulation containing the inventive vectors encoding the ts AAV Rep protein(s) may be administered to a cell by any means known in the art. In the case of viral vectors, the vector is typically introduced into the target cell by standard transduction methods.

Exemplary modes of administration of AAV-modified cells include, but are not limited to, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections.

Dosages will depend upon the mode of administration, the severity of the disease or condition to be treated, the individual subject's condition, the particular cell, and the gene to be delivered, and the species of the subject, the size and weight of the subject, and can be determined in a routine manner by those of skill in the art.

The invention will now be illustrated with reference to certain examples which are included herein for the purposes of illustration only, and which are not intended to be limiting of the invention.

EXAMPLE 1

Plasmids and Site Directed Mutagenesis

All recombinant DNA manipulations were performed following standard protocols (Ausubel et al., 1996, Current Protocols In Molecular Biology, vol. 3. John Wiley & Sons, New York). Unless otherwise noted, all enzymes were purchased from New England Biolabs and used according to supplier recommendations. The mutants used in this study were originally generated in the plasmid, pHIV-78 (Xiao, W., (1996), "Characterization of cis and trans elements essential for the targeted integration of recombinant adeno-associated virus plasmid vectors", Ph.D. Dissertation, University of North Carolina-Chapel Hill). pHIV-78 (FIG. 1B) is a derivative of pHIV-Rep (Antoni et al., (1991) *J. Virology* 65:396). pHIV-Rep contains a wild type rep gene and expresses all four Rep proteins from the HIV-LTR. To express Rep78 in the absence of the other rep gene products the splice site was modified to prevent splicing (spl–) and subsequent generation of the Rep68 and Rep40 proteins (Xiao, W., (1996), "Characterization of cis and trans elements essential for the targeted integration of recombinant adeno-associated virus plasmid vectors", Ph.D. Dissertation, University of North Carolina-Chapel Hill). In addition, the initiation codon following the p19 promoter was changed to GGG (Chejanovsky et al., (1989) *Virology* 173:120) to ablate expression of Rep52. For simplicity, the Rep78 protein expressed from pHIV-78 has been designated as the wild-type (wt) Rep78 control, with the recognition that the rep gene has been modified as described above.

Mutations were generated in the pHIV-78 construct using a vent polymerase site-directed mutagenesis procedure essentially as described previously (Byrappa et al., (1995) *Genome Research* 5:404) with an additional DpnI digestion step to remove the template DNA. DNA sequencing (UNC Sequencing Facility) confirmed point mutations. Regions immediately adjacent to the mutations were subcloned back into the original pHIV-78 vector backbone and sequenced to eliminate the possibility that additional mutations were introduced during PCR-mutagenesis.

Several of these mutations were also subcloned from pHIV-78 into an inducible bacterial expression vector, pStump68 (Young and Samulski, (2000) *J. Virology* 74:3953) that expresses the Rep68 protein. The Rep68 proteins contain a C-terminal 6×-His-tag (Rep68H6) for purification of the recombinant proteins over nickel columns. Subcloned mutations were confirmed by DNA sequencing, and inducible expression in *E. coli* was confirmed by Western blot analysis (data not shown).

The mutant D40,42,44A was also generated in the plasmid, pIM45, which contains the wt AAV genome without the terminal repeats as previously described (McCarty et al., (1991) *J. Virology* 65:2936). For clarity, these mutant rep proteins which are under the control of the p5 promoter will be designated as mutD40,42,44A to distinguish them from D40,42,44A-78 described in FIG. 1C. The mutD40,42,44A construct was generated by site-directed mutagenesis as previously described (Kyostio et al., *J. Virology* 68:2947) using the oligonucleotide 5' CCG CCA GCT TCT GCC ATG GCT CTG AAT 3' (SEQ ID NO:1). The pIM45 (wild-type) and mutD40,42,44A plasmids were used to produce virus from the plasmid pTRUF5, which contains the green florescent protein flanked by the AAV terminal repeats (Zolotukhin et al., (1996) *J. Virology* 70:4646) to generate the virus rAAV-UF5 (GFP). An additional recombinant adeno-associated virus (rAAV) plasmid, pAB-11, that was used in these studies has previously been described (Goodman et al., (1994) *Blood* 84:1492). Briefly, pAB-11 contains the β-galactosidase gene under the control of the cytomegalovirus (CMV) immediate-early promoter flanked by the AAV inverted terminal repeats.

EXAMPLE 2

Intracellular Replication Assays (IRA) and Viral Replication Time Course

Subconfluent 293 cells were cotransfected with mutant or wt pHIV-78 helper constructs and the rAAV plasmid (pAB-11) at a 3:1 molar ratio, respectively, via Lipofectin (Gibco/BRL) essentially as described in the supplier protocol. After 14 hours the DNA/lipofectin complexes were replaced with media containing enough adenovirus 5 (dl309, Jones et al., (1979) *Proc. Natl. Acad. Sci. USA* 76:3665) to infect cells at a MOI of 5. When transfections were performed to evaluate temperature sensitive activity of the mutants all reagents for transfection, including the cells and media, were prewarmed and incubated at the appropriate temperatures (32°, 37°, or 39° C.) following transfection. At 48 hours post infection (hpi), small molecular weight DNA was extracted (Hirt, (1967) *J. Mol. Biol.* 26:365), treated with RNaseA and digested extensively with DpnI to remove input plasmid DNA. Southern blots were performed on digested DNA (Ausubel et al., 1996, Current Protocols In Molecular Biology, vol. 3. John Wiley & Sons, New York) and probed with $^{32}$P-labeled β-galactosidase. Viral replication was determined by co-infecting subconfluent human embryonic kidney (HEK) 293 cells with rAAV-UF5 (MOI=5), adenovirus type 5 (MOI=5), and simultaneously transfecting with the mutD40A,D42A,D46A or pIM45 plasmids. Hirt DNA was analyzed using Southern blot and vector GFP specific probe.

EXAMPLE 3

Production of rAAV GFP Virus Using ts Rep Plasmids

In order to produce rAAV-UF5 virus HEK 293 cells were co-transfected by the CaPO$_4$ method as previously described (Stultz et al., (1997) Predicting protein structure with probabilistic models, in N. Allewell and C. Woodward 9ed.), Protein Structural Biology in Bio-Medical Research, vol. 22B. JAI Press, Greenwich) with pTRUF5 (Zolotukhin et al., (1996) *J. Virology* 70:4646), helper plasmid pXX6 to supply adenovirus functions (Xiao et al., (1998) *J. Virol.* 72:2224) and either wt pIM45 or mutD40,42,44A to supply rep functions. Following transfection the cells were incubated for 48 hrs, harvested, and subjected to three successive freeze/thaw cycles to liberate the virus. Incubations were performed at 32° C., 37° C. as well as 39.5° C. The crude viral preps containing rAAV-UF5 were then titrated by counting GFP single cell fluorescence.

EXAMPLE 4

Protein Methods

ECL/Western Blot

ECL/Western blots analyses were performed on transfected cell lysates essentially as recommended by the supplier (Amersham) and probed using a monoclonal antibody raised against all four of the AAV2 Rep proteins (Hunter et al., (1992) *J. Virology* 66;317).

Purification of Mutant and wt Rep68 His-tagged Fusion Proteins

His-tagged Rep68 fusion proteins (Rep68H6) were purified from SG13009 cells (Qiagen) by passage over nickel columns as previously described (Young and Samulski, (2000) *J. Virology* 74:3953) with minor modifications. Briefly, cleared cell extracts were incubated with Ni-NTA agarose (Qiagen) for 3–4 hrs at 4° C. followed by elution with a 0.1 to 0.5 M Imidazole linear gradient. Eluted proteins were analyzed by SDS-PAGE/silver stain (FIG. 4) according to the manufacture's protocol (Bio-Rad Silver Stain Plus). Protein concentrations were determined using the BCA kit (Pierce) with BSA as a standard and by direct comparison to known amounts of BSA on a silver stained SDS-PAGE gel.

EXAMPLE 5

DNA Substrates for in vitro Biochemical Assays

The AAV terminal repeat (TR) hairpin DNA used in the majority of the biochemical assays was prepared by EcoRI digestion of pDD (Xiao et al., (1997) *J. Virology* 71:941), generating a 171 bp DNA fragment with D sequences flanking either side of the TR (D' A C' C B' B A' D). The substrate was boiled and snap cooled to form a hairpin with a double stranded (ds) terminal resolution site (trs), and labeled with γ-$^{32}$P-ATP using T4 polynucleotide kinase (PNK) to generate the substrate, $^{32}$P-TR.

An AAV TR substrate with a single stranded (ss) trs region ($^{32}$P-TRss) was generated by digestion of psub201 (Samulski et al., (1989) *Cell* 33:135) with XbaI and PuvII as previously described (Im et al., (1989) *J. Virology* 63:3095), and labeled at the 5' end with PNK.

The DNA substrate for the helicase assays was generated by annealing a 24 base primer (NEB, #1224) to an M13 single stranded phage (United States Biochemical, #70704) essentially as described previously (Im et al., (1990) *Cell* 61:447). The substrate (M13/24) was labeled with α-$^{32}$P-dATP using the Klenow fragment of DNA polymerase in the presence of 0.5 mM dTTP and dGTP. For all substrates, the unincorporated nucleotides were removed by passage over G25 spin columns (Boehringer/Mannheim).

EXAMPLE 6

Electrophoretic Mobility Shift Assays

Electrophoretic mobility shift (EMS) assays were performed essentially as previously described (McCarty et al., (1994) *J. Virology* 68:4998). Briefly, 0.01–0.02 pmoles of $^{32}$P-TR were incubated with up to 9 ng (~0.15 pmoles) of mutant or wt Rep68H6 protein in 20 μL binding reactions (40 mM KCl, 10 mM HEPES-KOH (pH 7.5), 0.2 mM dithiothreitol (DTT), 5% (vol/vol) glycerol, and 0.5 μg BSA, and 1 μg of poly dIdC) at 25° C. for 30 min. Protein/DNA complexes were resolved on 5% non-denaturing polyacrylamide gels and quantitated using a phosphoimager.

EXAMPLE 7 trs Endonuclease Assays

Site-specific endonuclease activity was screened by trs endonuclease assays as previously described (Im et al., (1992) *J. Virology* 66:1119), except where indicated. Briefly, 20 μl reactions (25 mM Hepes-KOH (pH 7.5), 5 mM MgCl$_2$, 1 mM dithiothreitol (DTT), 0.4 mM ATP, 10 μg/ml BSA) containing 0.005–0.02 pmoles of $^{32}$P-TR (or $^{32}$P-TRss) and up to 9 ng (~0.15 pmoles) of mutant or wt Rep68H6 were incubated at 37° C. for 60 min. Reaction products were treated with protease K for 60 min, extracted with phenol:chloroform, precipitated and resolved on denaturing sequencing gels. The amount of product formed was determined using a phosphoimager.

EXAMPLE 8

Helicase Assays

The helicase assays (Im et al., (1990) *Cell* 61:447) were performed in the same reaction buffer as the trs endonuclease assay except where indicated. Briefly, 20 μl reactions containing 0.01–0.02 pmoles of M13/24 and up to 9 ng of mutant or wt Rep68H6 protein were incubated for 30 min at 37° C. Reactions were terminated by addition of 10 μl of stop solution (0.5% SDS, 50 mM EDTA [pH 7.5], 50% glycerol, 0.1% bromophenol blue, 0.1% xylene cyanole) and resolved by electrophoresis on a 5% non-denaturing polyacrylamide gels and quantitated using a phosphoimager.

EXAMPLE 9

Structural Modeling

Computational results were obtained using software programs from Molecular Simulations Inc. Dynamics calculations were performed with the DiscoverAE program, using the CFF91 forcefield, ab initio calculations were done with the DMol program, and graphical displays were printed out from the Cerius2 molecular modeling system.

EXAMPLE 10

Generation of Mutant and "Wild-Type" Rep78 Constructs

In an attempt to generate temperature sensitive (ts) Rep mutants we used a charged-to-alanine substitution strategy (Cunningham et al., (1989) *Science* 244:1081; Bennett et al., (1991) *J. Biol. Chemistry* 266:5191; Balague et al., (1997) *J. Virology* 71:3299) to target a number of the putative functional domains critical for Rep mediated activities (FIG. 1A). Site directed mutations were generated in a eucaryotic expression construct, pHIV-78 (Xiao, W., (1996), "Characterization of cis and trans elements essential for the targeted integration of recombinant adeno-associated virus plasmid vectors", Ph.D. Dissertation, University of North Carolina-Chapel Hill) that expresses only the 78 kDa AAV2 Rep protein (FIG. 1B). In this construct, the rep gene has been altered to prevent p19 protein expression (ATG converted to GGG) as previously described (Chejanovsky et al., (1989) *Virology* 173:120). In addition, the 5' splice site was inactivated so only the Rep78 protein initiated from the p5 promoter was expressed (as described in Example 1; Xiao, W., (1996), "Characterization of cis and trans elements essential for the targeted integration of recombinant adeno-associated virus plasmid vectors", Ph.D. Dissertation, University of North Carolina-Chapel Hill). For simplicity, we have designated the Rep78 protein expressed from pHIV-78 as the wild-type (wt) Rep78 control. Using intracellular expression, AAV mediated replication, and in vitro biochemical assays, the mutants described in FIG. 1C were grouped into three classes (Class I: non-ts and normal, Class II: ts for replication, and Class III: non-ts and defective for replication (Table 1).

TABLE 1

Summary of Rep Protein Mutations[a]

| Rep | Expression | Replication | Binding[b] | Nicking[b] | Helicase[b] |
|---|---|---|---|---|---|
| Class I (wild-type) | | | | | |
| Rep78 (wt) | + | + | + | + | + |
| E245A, D246 | + | + | ND[c] | ND | ND |
| K474A, D475A | + | + | ND | ND | ND |
| D519A, E521A | + | + | ND | ND | ND |
| I330C | + | + | ND | ND | ND |
| Y311F | + | + | + | + | + |
| E465A | + | + | + | + | + |
| D468A | + | + | + | + | + |
| E504A | + | + | +** | +** | +** |
| Class II (ts) | | | | | |
| D40, 42, 44A | +/−[d]* | +/−* | +[e] | +[e] | +[e] |

TABLE 1-continued

Summary of Rep Protein Mutations[a]

| Rep | Expression | Replication | Binding[b] | Nicking[b] | Helicase[b] |
|---|---|---|---|---|---|
| Class III | | | | | |
| D412A | + | +/− | + | +[f] | + |

[a]mutant proteins are designated by the site(s) of their amino acid changes.
[b]indicates assay was carried out with Rep68 protein
[c]ND, not determined.
[d]+/− indicates activity was less than 50% of wild-type (wt).
[e]activity present, but reduced as compared to wild-type
[f]indicates activity was sensitive to magnesium concentration
*indicates activity was sensitive to temperature.
**indicates activity required 50-fold more protein than wt.

EXAMPLE 11

Intracellular Expression of Mutant and wt Rep78 Proteins

Figure 2:
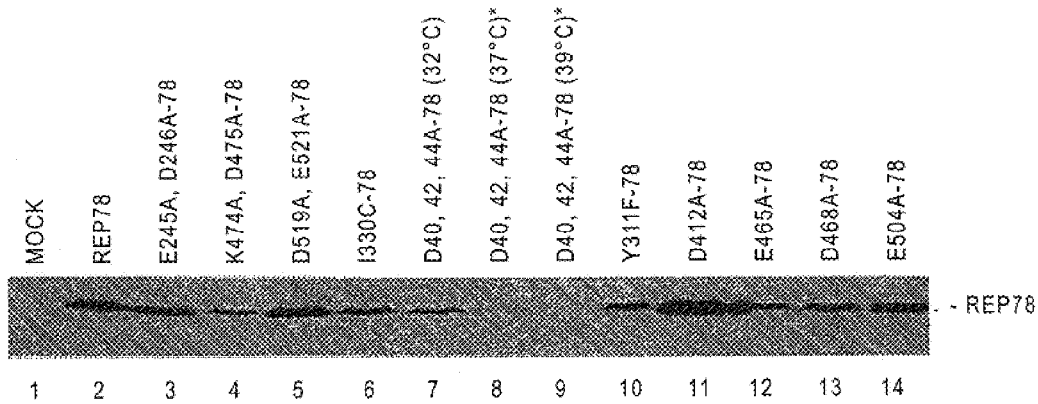
FIG. 2. Immunoblot analysis of the various Rep78 proteins expressed from the HIV-LTR in transiently transfected 293 cells. Mutant and wild type pHIV-78 constructs were transfected into 293 cells at 32° C., 37° C., and 39° C. as described in Example 11. A representative blot of protein expression is shown. With the exception of D40,42,44A all lysates were prepared from cells transfected at 37° C. Blots were hybridized with a monoclonal antibody that recognizes all four rep proteins. All lanes were loaded with 15 μl of cellular extract. *Proteins were detected after long term exposure of blots.

All of the mutant plasmids were sequenced and characterized for the ability to express full length Rep protein by transfection in 293 cells. Temperature sensitive (ts) expression was determined by transfecting mutant and wt pHIV-78 constructs into 293 cells at 32° C., 37° C. and 39° C. followed by Western blot analysis. A representative blot of protein expression is shown (FIG. 2). Based on protein expression at different temperatures, we designated two classes of Rep mutants. The class I mutant proteins were expressed at normal levels from the HIV-LTR promoter, whereas the class II mutant D40,42,44A-78 was present at levels below the detection sensitivity of the ECL/western blot analysis at 37° C. and 39° C. (FIG. 2, lanes 8 & 9). Expression of this Class II mutant was confirmed at 37° C. by overexposing Western blots (data not shown) and by comparing lysates prepared from cells transfected at 32° C. (FIG. 2, lane 7). Detection of the Class II mutant protein at 32° C., but not at 37° C. suggested a ts Rep phenotype (Diamond et al., (1994) *J. Virology* 68:863).

EXAMPLE 12

Replication Activity of Mutant Rep78 Proteins

Intracellular functional activity of the Rep mutants (FIG. 3A) and wt 78, 68, and a construct (wtRep) expressing all four Rep proteins (FIG. 3A, compare lanes 1, 14, and 15) was determined by assaying the ability to mediate replication of a recombinant AAV plasmid (pAB-11) in the presence of adenovirus. The replication activity of control plasmids expressing either wt Rep78 or 68 appeared equivalent (FIG. 3A, compare lanes 1, 14). The construct expressing all four rep proteins (labeled wtRep) generated slightly more replicated DNA in this assay as expected (FIG. 3A, compare lanes 1, 14, to 15). Mutants that had less than 50% of wtRep78 activity at 37° C. were considered to be defective for replication. Intracellular replication assays were also performed at 32° C. and 39° C. to determine if the rep mutants were ts in activity.

All of the class I mutants except D412A possessed replication activities that were similar to wtRep78 under physiological (FIG. 3A, lanes 2–5, 9 & 11–13) and non-physiological conditions (data not shown). The class II mutant, D40,42,44A-78, exceeded wtRep78 replication at 32° C., but was reduced over 3-fold at 37° C. and diminished to almost non-detectable levels at 39° C. (FIG. 3A, lanes 6–8). Both the temperature dependent expression and replication profiles for D40,42,44A-78 (FIG. 2, lane 7–9 and FIG. 3A, lanes 6–8), indicate that this variant had a ts phenotype.

In addition to assaying AAV replication with the ts mutant expressed from the HIV promoter cassette, the mutant was also assayed in the context of all the other AAV rep proteins (pIM45 helper construct, see Example 1). In these assays, replication was determined by Southern blots of Hirt extracts using a rAAV GFP vector (pTRUF5) for replication and GFP transduction for virus yield (FIG. 3B and Table 2, respectively). At 32° C., wt Rep demonstrated highest levels of replication at 36 hr, which diminished by 48 hr (FIG. 3B, 32° C. panel). At 32° C. the ts mutant was delayed at 24 hr but replication increased steadily and surpassed wt at the 48-hr time point. At the non-permissive temperature 39° C., the ts mutant was non-viable while wt Rep demonstrated normal levels of AAV replication at all time points (FIG. 3B). Virus yields for the ts mutant (mutD40,42,44A) at 32° C., 37° C. and 39° C. were $2.2 \times 10^6$, $3 \times 10^4$, and $3 \times 10^3$ transducing units/ml, respectively, thus displaying over a 3-log difference in titer between permissive and non-permissive temperatures (Table 2). From the above analysis, charge to alanine mutant D40,42,44A-78 displayed all of the characteristics of a temperature sensitive Rep protein.

After characterization of this ts mutant Rep protein, we turned our analysis to other variants that displayed a replication phenotype but did not appear to be temperature sensitive. The mutant D412A-78, which was originally identified as a Class I mutant Rep phenotype based on protein expression (FIG. 2, lane 11), had AAV replication activity 5 to 10 fold lower than wt Rep78 at all temperatures (FIG. 3A, lane 10 & data not shown). For this reason, D412A-78 was defined separately as a Class III mutant (normal protein levels, but decreased replication activity and not ts) and further analyzed.

In addition to the Class II and III mutants described in this replication assay, a high level of replication was mediated by three Class I mutant proteins, K474,D475A-78, Y311F-78 and E465A-78 (FIG. 3A, lanes 3, 9 and 11, respectively). These results are noteworthy considering that similar mutations at these positions have previously been shown to be negative for trs endonuclease activity when measured in vitro in the context of the MBP-Rep68Δ fusion protein (Davis et al., (1999) *J. Virology* 73:2084; Walker et al., (1997) *J. Virology* 71:2722).

TABLE 2

| | Yield[a] of rAAV-UF5 (GFP) Virus | | |
|---|---|---|---|
| Rep | 32° C. | 37° C. | 39.5° C. |
| pIM45 (wt[b]) | $9.4 \times 10^5$ | $1.7 \times 10^6$ | $6.8 \times 10^5$ |
| mutD40,42,44A[c] | $2.2 \times 10^6$ | $3.0 \times 10^4$ | $3.0 \times 10^3$ |

[a]transducing units/ml as described in the text.
[b]all four rep gene products expressed.
[c]mutations were generated in the pIM4 vector.

EXAMPLE 13

In vitro Expression and Purification of Mutant Rep Proteins

Figure 4:
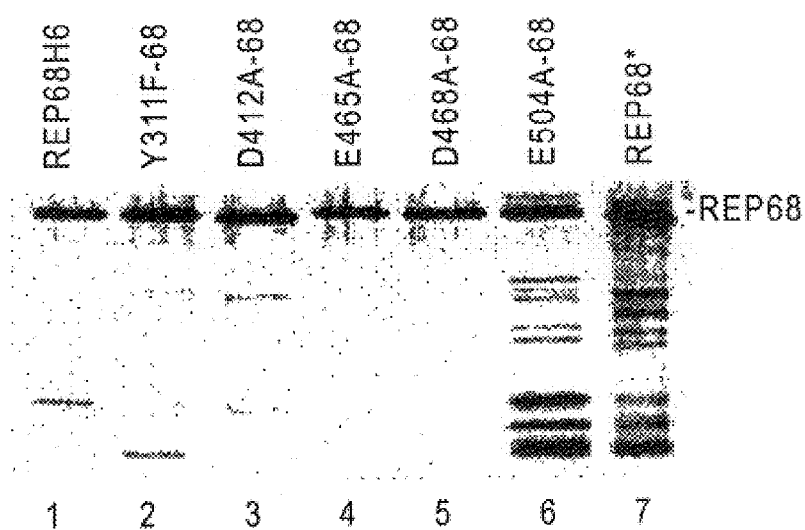
FIG. 4. SDS-PAGE/silver stain analysis of purified mutant and wt Rep68H6 proteins over expressed in *E. coli*. Proteins were expressed from the inducible expression cassette, pStump68, and purified via a 6XHis tag by passage over nickel-agarose columns (Qiagen) as described in Example 4. The position of full length Rep68H6 is indicated. The same amount of protein was loaded in each lane except E504A-68, which required 50-fold more protein to achieve the same level of full-length protein. The smaller molecular weight products visible in the gel (especially lanes 6 and 7) were degradation products as indicated by Western blot analysis (data not shown). Rep68* was expressed in a baculovirus system and purified as described previously (Im et al., (1989) *J. Virology* 63:3095).

In an effort to further characterize the non-ts Rep mutants described in the intracellular replication study, several mutant constructs (Y311F, D412A, E465A, D468A, and E504A) were subcloned into the bacterial expression vector, pStump68 (Young and Samulski, (2000) *J. Virology* 74:3953) for purification and characterized of Rep specific biochemical activities. The pStump68 construct allowed for high level expression and purification of Rep68 proteins from *E. coli* via a 6×His-tag fusion. Overexpression and purification from this vector enabled us to compare the activity of the mutant Rep proteins to well established biochemical activities previously assigned for wt Rep68 (Im et al., (1989) *J. Virology* 63:3095; Im et al., (1990) *Cell* 61:447; Im et al., (1992) *J. Virology* 66:1119). Silver stained SDS-PAGE gels (FIG. 4) and Western blot analysis (data not shown) demonstrated that the 6×His-tagged proteins were purified to greater than 95% homogeneity. With the exception of mutant E504A-68, the Rep mutants expressed similar amounts of stable Rep68 protein (FIG. 4). Mutant E504A-68 required 5× more total protein when assayed under these conditions and appeared to have a pronounced profile of breakdown products that were similar to Rep68 purified from baculovirus (FIG. 4, lanes 6 and 7). This was in contrast to its expression in 293 cells which appeared normal (FIG. 2, lane 14). These two contradicting data suggest that this mutant may be unstable in the context of the His-tagged fusion protein. While this result exemplifies the concern of modifying Rep for *E. coli* expression, all other constructs generated identical protein profiles both in vivo and in vitro supporting further analysis of their biochemical activities.

EXAMPLE 14

Interaction of Rep68H6 Proteins with the AAV TR

Figure 5:
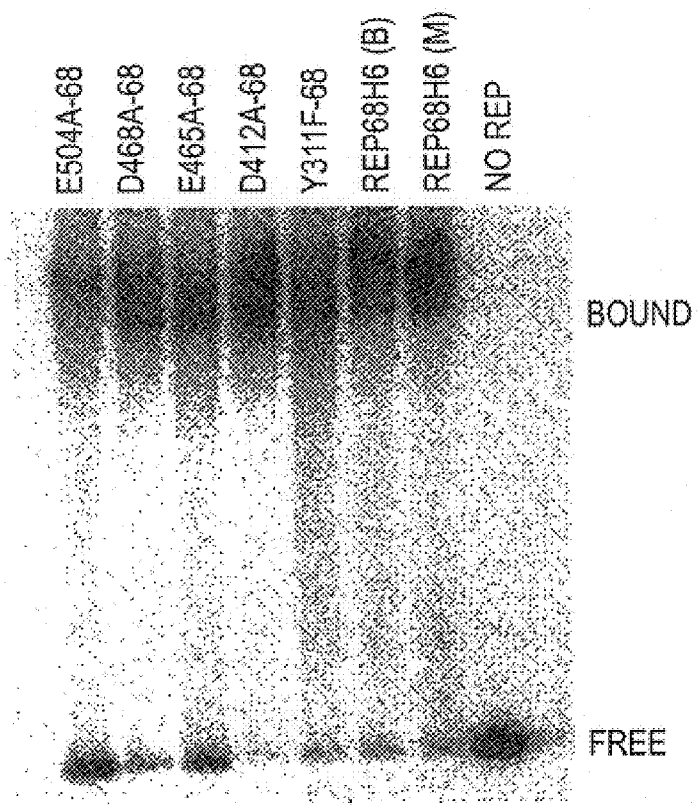
FIG. 5. In vitro biochemical analyses of His-tagged Rep68 proteins. Panel A. Gel mobility shift assay of mutant and wt Rep68H6 proteins expressed in *E. coli*. Standard binding reactions contained 0.5 nM $^{32}$P-labeled AAV terminal repeat hairpin DNA ($^{32}$P-TR) and 6 nM purified Rep68 protein containing the indicated mutation. Reactions were carried out in standard binding reaction buffer (see Example 6) at 25° C. for 30 min and resolved on non-denaturing 5% polyacrylamide gels. Mutant and Rep68H6 (B) proteins were purified by one time passage over nickel columns (Batch) while, Rep68H6 (M) was further purified by passage over a mono Q column. Panel B. Terminal resolution by His-tagged Rep68 proteins. Standard trs endonuclease assays contained 0.5 nM of $^{32}$P-TR substrate and 5 nM His-tagged protein. Nicking reactions were performed in standard nicking buffer (see Example 7) for 60 min at 37° C., followed by protease K digestion, and phenol:chloroform extraction, and resolved on denaturing polyacrylamide sequencing gels. Substrate (S) and cleavage products (P) are indicated. Panel C. Standard helicase reactions were performed at 37° C. for 60 min in nicking buffer containing 0.5 nM substrate (M13/24) and 6 nM protein and resolved on 5% non-denaturing polyacrylamide gels. Substrate (S) and released product (P) are indicated. Boiled, positive control. In all of the assays described for FIG. 5, E504A-68 required 50-fold more protein to achieve the level of activity shown.
Figure 5:
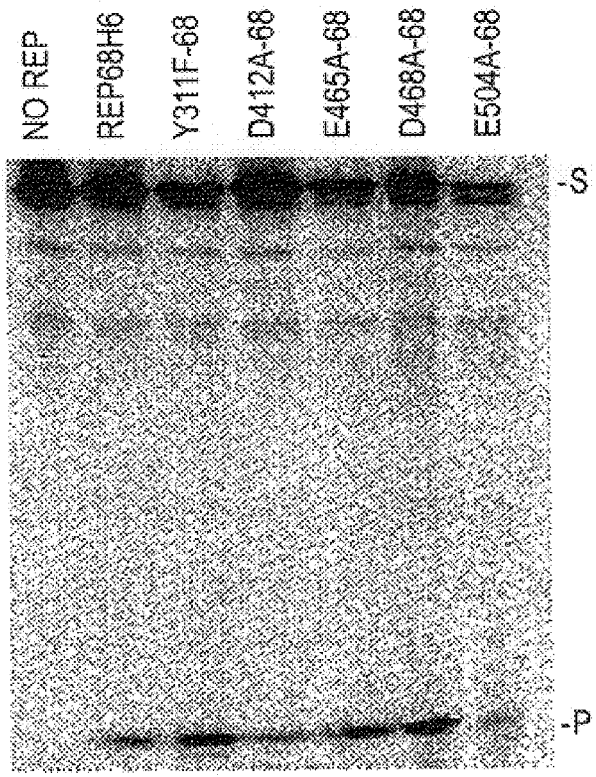
Figure 5:
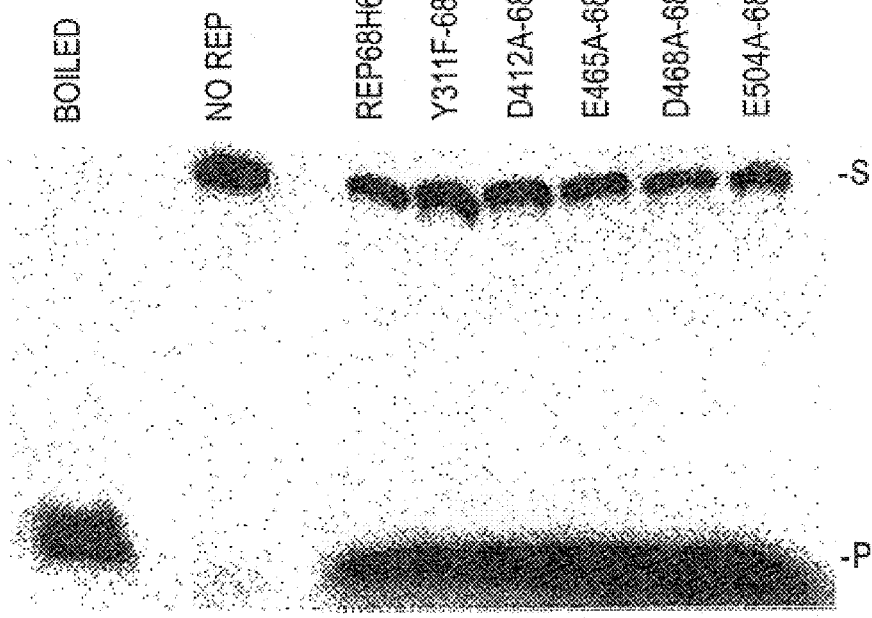

Standard mobility shift assays were used to compare the specific binding of mutant and wt Rep68H6 proteins to the hairpin TR substrate ($^{32}$P-TR). Binding titration profiles performed with each class of mutant protein were similar to wt Rep68H6 (data not shown). A representative binding assay with a protein to DNA molar ratio of ~10:1 demonstrated that all of the His-tagged *E. coli* produced proteins bound specifically to $^{32}$P-TR (FIG. 5A). Specific binding to the TR suggested that neither the point mutations nor the addition of the 6×His-tag significantly altered the DNA binding activity of these Rep68 proteins. However, as observed in the silver stain analysis, approximately 50-fold more total protein was used in the binding assays for E504A-68 relative to wt Rep68H6.

EXAMPLE 15

Effect of Mutations on Rep68H6 trs Endonuclease Activity

Site-specific and strand specific endonuclease cleavage by Rep78/68 of the AAV TR is an essential part of AAV replication (Muzyczka, (1992) *Current Topics in Microbiology and Immunology* 158:97). All of the mutants examined specifically nicked the TR at the trs generating the proper sized product (FIG. 5B). In the nicking assay shown (FIG. 5B) a protein to DNA molar ratio of ~10:1 was used for all of the mutants except E504A-68, which required ~50 fold more total protein to obtain the same level of cleaved product.

Also of interest was the wild-type level of cleavage observed with the mutants Y311F-68 and D465A-68 (FIG. 5B). From previous published studies, mutants at these positions were not expected to display nicking activity (Walker et al., 91997) *J. Virology* 71:2722). We suspect that the discrepancy between our analysis and others concerning in vitro biochemical activities (id.), are related to the MBP-Rep68 fusion protein. With the exception of mutant E504A-68, we did not observe an influence on Rep activity in the context of the Rep68H6 protein. In addition, these same mutants when expressed from the HIV-LTR promoter cassette in vivo without the His modification, all displayed AAV replication activity supporting the in vitro biochemical analysis.

EXAMPLE 16

Effect of Mutations on Rep68H6 Helicase Activity

Under the reaction conditions used in these assays (~10:1 protein to DNA molar ratio) all of the Rep68H6 mutants examined exhibited helicase activity (FIG. 5C).

Figure 3:
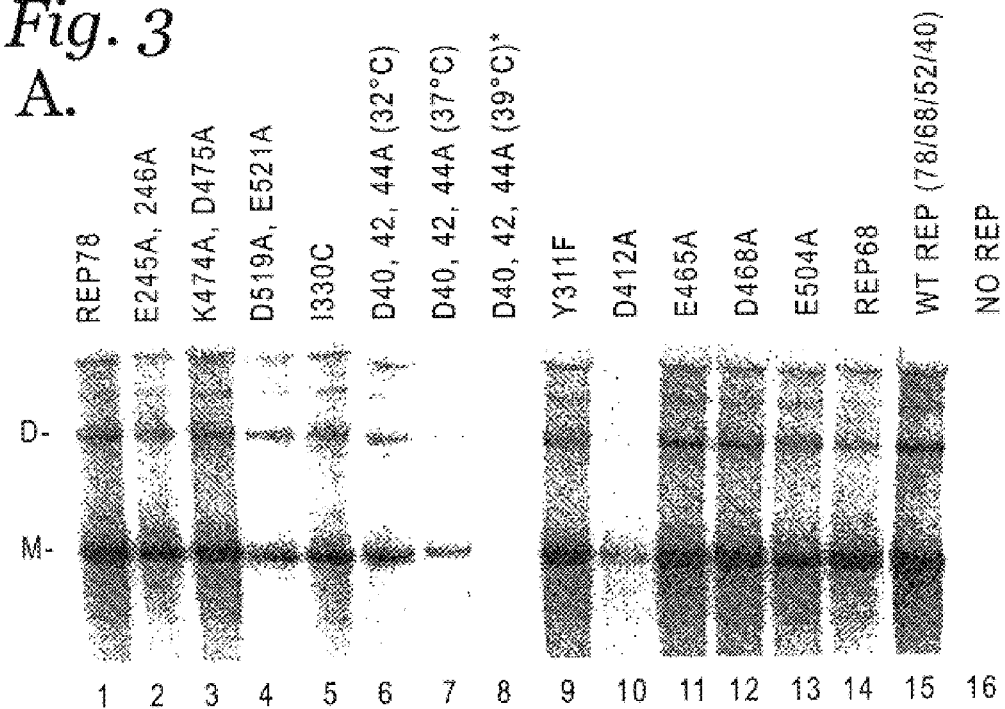
FIG. 3. Southern blot analysis of intracellular replication mediated by various Rep78 proteins. Panel A. Representative Southern blot of rAAV-LacZ (pAB-11) replication mediated by mutant and wt Rep78 proteins expressed from the HIV-LTR in Ad5 infected 293 cells. The replication assays shown were performed at 37° C., except as indicated for D40,42,44A (lanes 6–8). The pHIV-78 and pAB-11 constructs were transfected at a 3:1 molar ratio as described in Example 12. Following transfection the cells were incubated for 48 hrs with Ad5 (MOI of 5). At 48 hpi Hirt DNA was extracted, digested with DpnI, and analyzed by southern blot using a $^{32}$P-labeled probe specific for β-galactosidase sequences. Replicative monomer (M) and dimer (D) DNA forms are indicated. *Replicated forms of pAB-11 were detected only after long term exposure of blots. Rep68 was expressed from pHIV-68, a derivative of the pHIV-78 construct that has the rep gene intron removed as described (Xiao, W., (1996), "Characterization of cis and trans elements essential for the targeted integration of recombinant adeno-associated virus plasmid vectors", Ph.D. Dissertation, University of North Carolina-Chapel Hill). Wt Rep is expressed from the pHIV-Rep construct that expresses all four rep gene products as described in methods. Panel B. Southern blot analysis of replication of a rAAV-UF5 virus (GFP) mediated by transfected wt pIM45 or mutD40A, D42A,D44A pIM45 rep expression plasmids. The pIM45 constructs express all four rep gene products (see Example 1). Transfection/infections were performed at permissive (32° C.) and non-permissive (39.5° C.) temperatures in Ad5 infected HEK 293 cells. Rep containing plasmids (wt pIM45 or mutD40,D42,D44A pIM45) were transfected into sub-confluent HEK 293 cells and simultaneously co-infected with Ad5 (MOI 5) and rAAV-UF5 (MOI 5). At various time points Hirt DNA was extracted and analyzed by Southern blot as described above using a $^{32}$P-labeled probe specific for GFP sequences. No plasmid lanes: cells were infected with Ad5 only, pIM45 (wt) lanes: cells were co-infected with Ad5 and rAAV-UF5, and transfected with wt pIM45; mutD40,42,44A lanes: cells were co-infected with Ad5 and rAAV-UF5, and transfected with mutD40,D42,D44A pIM45.
Figure 3:
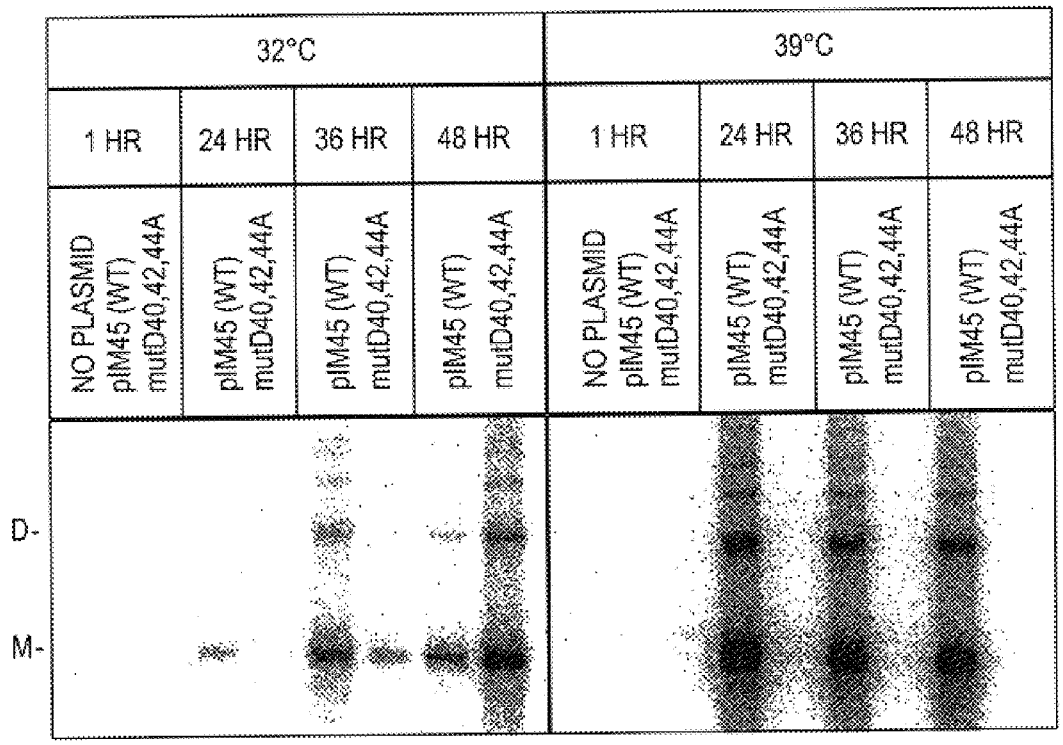

Retention of nicking and helicase activities by D412A-68 was somewhat surprising considering that this mutant was notably defective in the intracellular replication assay (FIG. 3, lane 10). In an effort to assign a phenotype to the D412A mutation, more comprehensive biochemical analyses were conducted comparing the activity of D412A-68 to wt Rep68H6.

EXAMPLE 17

Affinity of D412A-68 vs Rep68H6 for the Hairpin TR

Figure 6:
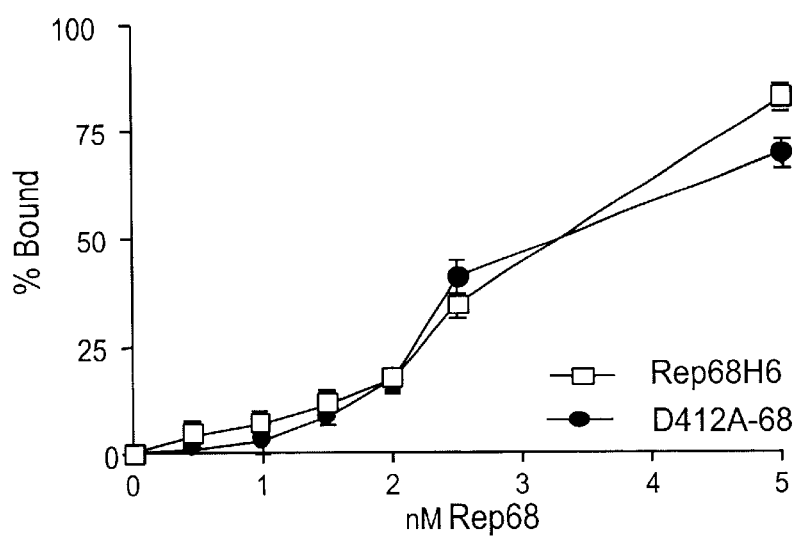
FIG. 6. Binding, trs endonuclease and helicase activities of D412A-68 and Rep68H6 as a function of protein concentration. Panel A. Standard binding reactions were performed as described in FIG. 5A with 1 nM substrate ($^{32}$P-TR) and the indicated concentration of each protein. Panel B. Standard nicking reactions were performed as described in FIG. 5B and contained 1 nM $^{32}$P-TR substrate and the indicated concentration of each protein. Panel C. Standard helicase reactions were performed as described in FIG. 5C in nicking buffer containing 1 nM substrate (M13/24) and the indicated concentration of protein.
Figure 6:
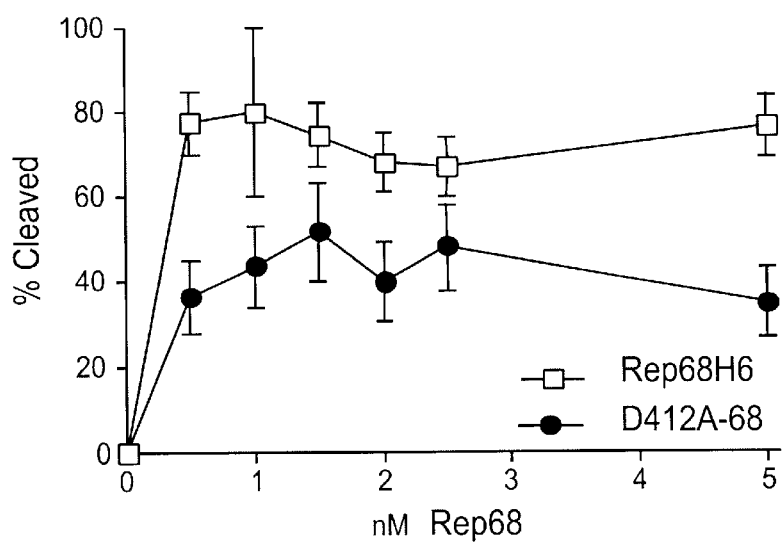
Figure 6:
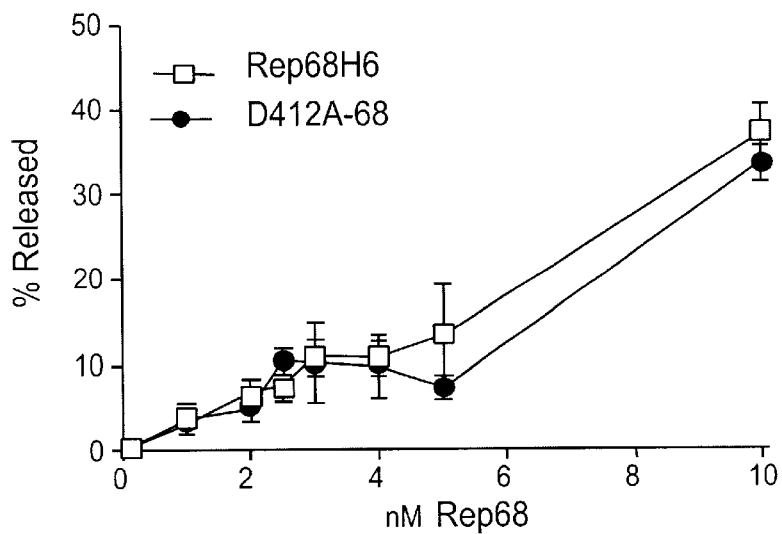

In the assays described above, a difference in binding between D412A-68 and wt Rep68H6 was not detected. This suggested that the replication defect observed with D412A-78 in the intracellular assays was not due simply to an inability to interact efficiently with the viral TR. While we used 500 fold less Rep protein compared to other studies (Walker et al., (1997) *J. Virology* 71:2722), we still had excess protein relative to the TR concentration potentially masking any subtle differences in binding efficiency. In order to determine the concentration of D412A-68 and wt Rep68H6 required to bind 50% of the substrate ($K_D$), binding assays were performed with excess $^{32}$P-TR substrate. The apparent $K_D$ values were determined from plots of the percent of TR bound vs protein concentration (FIG. 6A). The apparent $K_D$ values for wt Rep68H6 and D412A-68 for the TR were essentially the same at about ~3 nM (FIG. 6A). These values were also within the nM range previously described for baculovirus purified Rep68 binding to a hairpin TR substrate (McCarty et al., (1994) *J. Virology* 68:4998).

EXAMPLE 18

Titration of trs Endonuclease and Helicase Activity

In an effort to identify gross biological differences between the mutant and wt Rep, protein levels were in excess relative to the respective DNA substrates. In the following assays, the efficiency of D412A-68 compared with wt Rep68H6 in the trs endonuclease, and helicase activity was determined with the nicking and helicase substrates in excess (FIGS. 6B and 6C, respectively). In the nicking assay comparisons, nearly 3-fold more D412A-68 protein was required to nick 50% of the substrate, and about 25% less substrate was cleaved overall relative to wt Rep68H6 (FIG. 6B). In contrast, no significant differences were observed between the efficiency of D412A and wt Rep68H6 in the helicase assay (FIG. 6C).

EXAMPLE 19

Effect of Magnesium Concentration on Rep68 Functions

Figure 7:
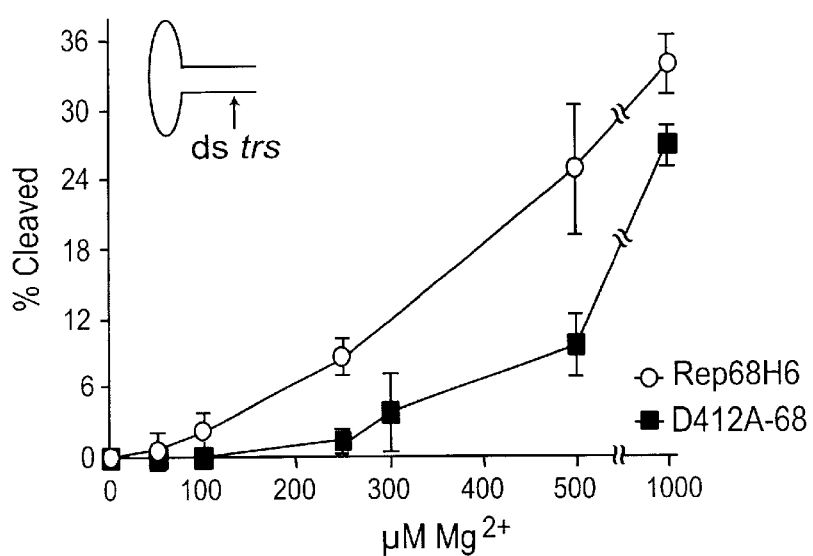
FIG. 7. trs endonuclease and helicase activity of D412A-68 and Rep68H6 as a function of magnesium concentration [$Mg^{2+}$]. Panel A. Endonuclease reactions were performed as described in FIG. 5B. Nicking buffer contained 1 nM substrate ($^{32}$P-TR) with a double-stranded nicking site (trs), 3 nM protein and the indicated [$Mg^{2+}$]. Panel B. Helicase assays were performed as described in FIG. 5C in nicking buffer that contained 1 nM helicase substrate (M13/24), 3 nM protein and the indicated [$Mg^{2+}$]. Panel C. Nicking reactions were performed as described in FIG. 5B. Nicking buffer contained 1 nM substrate ($^{32}$P-TRss) with a single-stranded nicking site (trs), 3 nM protein and the indicated [$Mg^{2+}$].
Figure 7:
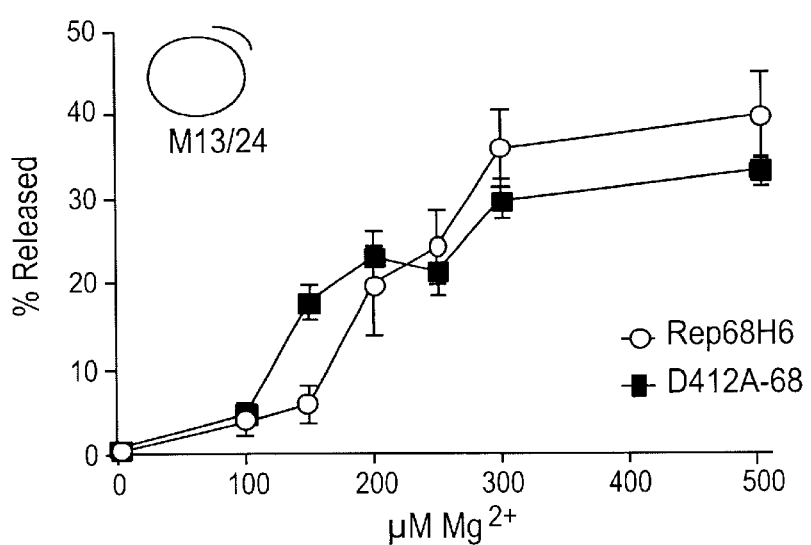
Figure 7:
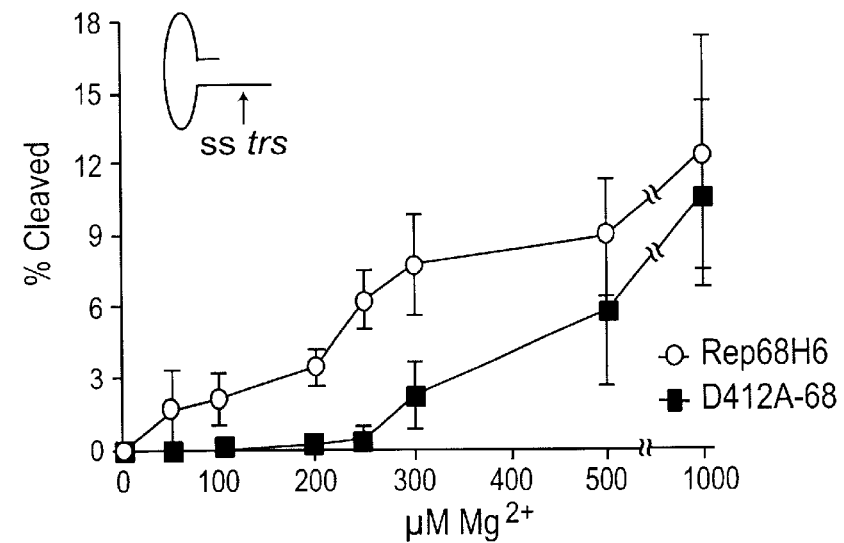

Previous studies have shown that the endonuclease activity of Rep68 requires magnesium ($Mg^{2+}$) (Im et al., (1990) Cell 61:447). In the nicking reactions described above, the $Mg^{2+}$ concentration [$Mg^{2+}$] was held constant at 5 mM, which is approximately 10-fold greater than would be present in the intracellular environment (Alberts et al., 1989, Molecular Biology of the Cell, $2^{nd}$. ed. Garland Publishing, Inc., New York). Under such conditions if an interaction between $Mg^{2+}$ and Rep68 were necessary to form an active transition state for nicking, a difference in binding affinity for $Mg^{2+}$ might go unnoticed. Excess $Mg^{2+}$ in the nicking reactions should shift the equilibrium in favor of binding, therefore potentially masking a mutant protein phenotype. For this reason, nicking reactions were performed under conditions of limited [$Mg^{2+}$] (FIG. 7A). Neither of the proteins were very efficient at nicking the TR when the [$Mg^{2+}$] was <500 $\mu$M. However, wt Rep68H6 activity increased linearly with [$Mg^{2+}$] and cleaved about 14-fold more substrate at 250 $\mu$M $Mg^{2+}$. In contrast, we could not detect any cleaved substrate with D412A-68 at <200 $\mu$M $Mg^{2+}$. The sensitivity to [$Mg^{2+}$] with D412A-68 suggested that this mutant had a diminished ability to bind $Mg^{2+}$ and that an interaction between $Mg^{2+}$ and D412 was necessary for efficient trs endonuclease activity in vitro.

In addition to requiring $Mg^{2+}$ for endonuclease activity, Rep also requires the ATP-dependent helicase activity to nick the viral TR (Snyder et al., (1993) J. Virology 67:6096). The Rep helicase activity was suggested to be necessary to unwind the double stranded TR in order to expose the terminal resolution site (id.). This function also requires $Mg^{2+}$ (Im et al., (1990) Cell 61:447). Thus, the sensitivity to [$Mg^{2+}$] in the above nicking assays could also reflect an impairment of helicase activity. To address this possibility we titrated [$Mg^{2+}$] levels in a Rep dependent helicase assay previously described (id.). From this analysis, D412A-68 and wt Rep68H6 had similar $Mg^{2+}$ requirements in the helicase assay (FIG. 7B).

To further demonstrate that the $Mg^{2+}$ dependence of the Class III mutant D412A was related to Rep's trs endonuclease activity and not related to helicase function, we performed TR nicking assays using a modified TR substrate. Previously Snyder et al., (1993) J. Virology 67:6096, generated a TR substrate with the nicking site (trs) existing as a single stranded (ss) DNA. These authors were able to demonstrate wt Rep nicking activity in the absence of ATP suggesting that the helicase function to expose the nicking site was not required. We performed identical nicking assays with the D412A mutant Rep and demonstrated that the amount of cleaved product using this ss substrate ($^{32}$P-TRss) was also sensitive to $Mg^{2+}$ levels (FIG. 7C). This data supports the role of Rep amino acid D412 in $Mg^{2+}$ binding, and suggests that this interaction is important in AAV trs endonuclease activity.

EXAMPLE 20

Instability of the pHIV-78 Construct

The ts Rep78 mutant described in the preceding Examples was originally generated in the plasmid, pHIV-78. pHIV-78 is a derivative of pHIV-Rep (Mendelson et al., (1986) J. Virology 60:823) that contains the wild type rep genes and expresses all four Rep proteins from the HIV-LTR. To express the Rep78 protein in the absence of the other rep gene products, the splice site was mutated (spl–) to prevent splicing and subsequent generation of the Rep68 and Rep40proteins. In addition, the initiation codon following the p19 promoter was changed ($\Delta$p19) to GGG to ablate expression of Rep52 and Rep40. The stability of the ts Rep78 protein was found to be very low at 37° C. and 39° C. in the pHIV-78 construct, but not when the ts mutation (D40,42,44A) was located on the wt plasmids pIM45 or pSSV9 (expressing all four rep proteins).

This discrepancy may be significant because for certain applications using the ts Rep mutations, it would be advantageous for the ts Rep protein to be labile as well as inactive at non permissive temperatures. It has been reported that even low levels of Rep protein have cytopathic effects. The ts Rep would perform its functions at permissive temperatures, and any Rep that was expressed at non-permissive temperatures would be labile and turn over rapidly. However, if the ts Rep is to be used in a helper virus to generate recombinant AAV vectors, the other rep proteins would most likely need to be present. In this situation, it may not be feasible to use the pHIV-78 construct, unless the other proteins would need to be supplied in trans. Thus, we set out to determine what element(s) are contributing to the instability of the ts Rep78 protein so that we may capitalize on these aspects of the protein.

We first considered the possibility that one of the other three Rep proteins was interacting with the ts Rep78 and stabilizing it in when expressed from the wt plasmid (pIM45). This was tested by cotransfection experiments in which plasmids that express each of the individual rep proteins (pHIV-68, pHIV-52, pHIV40) were co-transfected 293 cells along with the ts pHIV-78 construct (pD40,42, 44A-78). Western blots demonstrated that none of these proteins were able to stabilize the tsRep78 in trans at 37° C. or 39° C.

These results suggested that one or more of the other cis mutations within tsRep78 (spl– and/or $\Delta$p19) were contributing to the instability of the ts Rep78 protein. This construct contains not only the three aspartic acid (40,42,44) to alanine changes, but also the Met to Gly change at p19 (AT to GG change at nt 993–994 of the AAV genome, corresponding to nt 1836–1837 of pHIV-78) and two amino acid changes at the splice donor site (GT to CA change at nt 1907–1908 of the AAV genome, corresponding to nt 2750–2751 of pHIV-78, to prevent splicing results in an R to S and Y to N mutation). How these additional changes affect the global folding and stability of the ts Rep protein is not clear. The nucleotide sequences at these sites are conserved across the AAV serotypes, with the exception, that the sequence at the 5' splice donor site for AAV6 is CT except GT for AAV5. The nucleotide and amino acid positions of the p19 start site and 5' splice donor site is as described hereinabove and in, e.g., Chiorini et al., (1999) J. Virology 73:1309; international patent publication WO 00/28061 to Wilson et al.

Hence, experiments are carried out to determine which cis element of the ts pHIV-Rep78 construct affects its stability. A collection of constructs was created in which one or more of the cis mutations are present in the rep gene along with the ts mutations (D40,42,44A). These constructs were generated in both the pSSV9 (wt virus) and the pHIV (rep only) plasmid backgrounds. For the pSSV9 constructs the ts mutations were cloned into the wt plasmid at the PpuMI/BamHI sites, ts-V9. The Δp19 mutations were subcloned from pHIV-78 into the BamHI/HindIII site of ts-V9, to generate ts-V9/Δp19. The spl– mutations were cloned from pHIV-78 into the SalI/SwaI sites of ts-V9, to generate ts-V9/spl–. For the pHIV constructs we are using a number of different clones: the plasmids pHIV-Rep (wt rep gene), pHIV78/68 (Δ19) and pHIV-78/52 (spl–).

Each of the plasmids, along with the tsRep78 construct, was digested with BamHI and AseI yielding 2.5 kb and 5.2 kb fragments. The 5.2 kb fragments containing either the Δp19 or spl– mutations (or wt in the case of pHIV-Rep) were ligated to the 2.5 kb fragment from tsRep78. These ligations generated a series of constructs that contain the ts mutation along with an otherwise wt rep gene (tsRep), or with the p19 mutation (tsRep/Δp19), or with the splice minus mutation (tsRep/spl–).

These constructs are screened for proper rep gene expression and their influence on the stability of the ts Rep proteins at 32, 37 and 39° C. These constructs are also screened for their ability to mediate targeted integration of a recombinant AAV vector into the AAVS1 site of chromosome 19.

In addition, a collection of constructs are made that lack the ts Rep mutations (D40,42,44A) to determine whether these mutations are associated with increased turnover in the absence of the ts Rep mutations. These constructs are screened for stability of the expressed Rep protein at 32, 37 and 39° C., as well as for mediation of targeted integration.

EXAMPLE 21

Use of the tsRep to Generate a Helper Adenoviruses to Generate AAV Vector

Current techniques for packaging AAV vectors are not readily amenable to large-scale production. These difficulties arise, in part, from toxicity of the AAV rep proteins to helper viruses and host cells, thus requiring that the AAV rep/cap genes be provided on a separate vector from the helper virus or silenced in the cell chromosome. An adenovirus vector expressing the ts Rep proteins may overcome these limitations.

To this end, the ts mutations (D40,42,44A) from pHIV-78 were subcloned into the PpuMI/BamHI site of pSSV9 as described above. This construct was confirmed by sequencing and the XbaI fragment was obtained, blunt ended with T4 DNA polymerase, and subcloned into the ClaI/PvuII sites of pAdlox (Hardy et al., (1997) *J. Virology* 71:1842), to generate pts-V9-Ad. This construct was used to generate recombinant Ad in cre-recombinase expressing cells (CRE8 cells; Hardy et al., (1997) *J. Virology* 71:1842). This construct has all of the elements necessary to provide the helper functions for rAAV production.

Adenovirus is then subjected to double-plaque-purification. This step should eliminate any wt virus contamination. The viruses are grown at 39° C. to limit Rep activity. Western blot analyses demonstrated that all four Rep proteins were stably expressed at the time the viruses were passed for plaque purification, thus the instability of the ts protein is lost in this context, as expected. Southern blots showed that the rep gene was present in the adenovirus clones. This finding suggests that the Rep78 and Rep 68 proteins being expressed are not active enough at 39° C. to prevent adenovirus replication or result in a deletion of the rep gene.

Following double-plaque purification, these viruses are screened for the ability to mediate production of pAdlox plasmid carrying a rAAV genome encoding the Green Fluorescent Protein (TR-GFP; Zolotukhin et al., *J. Virology* 70:4646) at permissive and non-permissive temperatures.

EXAMPLE 22

Use of Adenovirus Vectors Containing the ts Rep78 Gene in Tandem with a TR Containing rAAV Genome (GFP-TR) for Targeted Integration of rAAV Vectors A hybrid adenovirus vector containing the ts Rep78 protein may be used to perform ex vivo integration at permissive temperatures.

Briefly, the ts rep mutations from the SspI to SwaI sites of pHIV-78 were subcloned into the PvuII site of Adlox vector to generate pts78-Ad. This has a dual purpose (1) to determine if the adenovirus is more tolerant of the more labile rep protein (this construct has all of the additional mutations as described in Example 20), and (2) to generate a chimeric adenovirus that contains not only rep but a rAAV vector as well.

Four separate clones of the ts78-Ad virus are generated in cre-recombinase expressing cells by the vector core facility at the University of North Carolina at Chapel Hill, and individual plaques are purified.

To generate chimeric virus, the PvuI/AseI fragment from pEGFP (GFP gene under control of a CMV promoter, flanked by AAV ITRs; a gift from Rebecca Haberman) was ligated into the SmaI site of all four pts78-Ad constructs described above. These constructs are sequenced to verify the insertion was ligated in correctly, and are used to generate recombinant adenovirus as describe in Example 21. Adenovirus is subjected to double-plaque purification, and Western and Southern blots are carried out to determine whether the rep gene was present in the adenovirus, also as described in Example 21. The results of these analysis suggests that the rep gene was stably expressed by the hybrid adenovirus construct.

Cultured human cells (e.g., hematopoietic progenitor cells or HeLa cells) are infected with the chimeric ts78-Ad carrying the AAV ITR-GFP transgene cassette at a permissive temperature of 32° C. The cells are maintained at 32° C. for a suitable temperature under conditions sufficient for integration of the ITR-GFP sequences. The infected cells are then shifted to 39° C. for a sufficient time to inactivate the tsRep proteins. Controls are kept at the non-permissive temperature for the entire experiment. Integration into chromosome 19 can be determined by known methods, e.g., by PCR amplification of the AAV-chromosome 19 junction regions (Samulski et al., (1991) *EMBO J* 10:3941 (published erratum appear at *EMBO J.* (1992) 11:1228).

Although the foregoing invention has been described in some detail by way of illustration and example for purposes of clarity of understanding, it will be obvious that certain changes and modifications may be practiced within the scope of the appended claims.

That which is claimed is:

1. A nucleotide sequence encoding a temperature-sensitive adeno-associated virus (AAV) Rep protein wherein said AAV Rep protein is a Rep78 or Rep68 protein, and wherein said AAV Rep protein comprises a mutation in the amino-terminal half from amino acid positions 25 to 75, wherein said mutation confers a temperature sensitive phenotype to said AAV Rep protein.

2. The nucleotide sequence of claim 1, wherein said nucleotide sequence encodes a temperature-sensitive AAV Rep78 protein and a temperature-sensitive AAV Rep68 protein.

3. The nucleotide sequence of claim 2, wherein said nucleotide sequence further encodes an AAV Rep52 protein and an AAV Rep40 protein.

4. The nucleotide sequence of claim 1, wherein said nucleotide sequence further encodes the AAV Cap proteins.

5. The nucleotide sequence of claim 1, wherein said nucleotide sequence further comprises an AAV template comprising (i) an AAV inverted terminal repeat, and (ii) a heterologous nucleotide sequence.

6. The nucleotide sequence of claim 5, wherein said heterologous nucleotide sequence encodes a peptide or protein.

7. The nucleotide sequence of claim 5, wherein said heterologous nucleotide sequence is flanked by 5' and 3' AAV inverted terminal repeats.

8. The nucleotide sequence of claim 1, wherein said nucleotide sequence comprises an expression control element operably-associated with the coding sequences for said temperature-sensitive AAV Rep protein.

9. The nucleotide sequence of claim 8, wherein said expression control element is an AAV p5 promoter.

10. The nucleotide sequence of claim 8, wherein said expression control element is an inducible expression control element.

11. The nucleotide sequence of claim 1, wherein said nucleotide sequence comprises:
    (a) a rep coding sequence encoding a temperature-sensitive AAV Rep78 protein and a temperature sensitive Rep68 protein, and
    (b) a heterologous nucleotide sequence flanked by 5' and 3' AAV inverted terminal repeats,
    wherein said rep coding sequence is not flanked by said AAV inverted terminal repeats.

12. The nucleotide sequence of claim 11, wherein said rep coding sequence of (a) further encodes a Rep52 protein and a Rep40 protein.

13. The nucleotide sequence of claim 11, wherein said nucleotide sequence further comprises a cap coding sequence encoding the AAV Cap proteins, wherein said cap coding sequence is not flanked by said AAV inverted terminal repeats.

14. The nucleotide sequence of claim 1, wherein said AAV Rep protein is a heat sensitive AAV Rep protein.

15. The nucleotide sequence of claim 1, wherein said AAV Rep protein is selected from the group consisting of AAV type 1, AAV type 2, AAV type 3, AAV type 4, AAV type 5, and AAV type 6 Rep proteins.

16. The nucleotide sequence of claim 15, wherein said AAV Rep protein is an AAV type 2 Rep protein.

17. The nucleotide sequence of claim 1, wherein said AAV Rep protein is an AAV Rep78 protein.

18. The nucleotide sequence of claim 1, wherein said AAV Rep protein is an AAV Rep68 protein.

19. A nucleotide sequence encoding a temperature-sensitive adeno-associated virus (AAV) Rep protein wherein said AAV Rep protein is a Rep78 or a Rep68 protein, and further wherein said AAV Rep protein comprises one or more mutations selected from the group consisting of:
    (a) a mutation at amino acid position 40,
    (b) a mutation at amino acid position 42, and
    (c) a mutation at amino acid position 44,
    wherein said one or more mutations confer a temperature sensitive phenotype to said AAV Rep protein.

20. The AAV Rep protein of claim 19, wherein said one or more mutations are missense mutations.

21. The AAV Rep protein of claim 19, wherein said one or more mutations are missense mutations that result in the substitution of an uncharged amino acid for a charged amino acid.

22. The AAV Rep protein of claim 19, wherein said AAV Rep protein comprises mutations at amino acid positions 40, 42 and 44 of the AAV type 2 Rep protein.

23. The AAV Rep protein of claim 22, wherein said AAV Rep protein comprises a mutation that results in the substitution of an alanine at amino acid positions 40, 42 and 44 of the AAV type 2 Rep protein.

24. The nucleotide sequence of any of claim 19, 22 or 23, wherein said AAV Rep protein is an AAV Rep78 protein.

25. The nucleotide sequence of any of claim 19, 22 or 23, wherein said AAV Rep protein is an AAV Rep68 protein.

26. A vector comprising the nucleotide sequence of any of claim 1, 19, 22 or 23.

27. The vector of claim 26, wherein said vector is a plasmid vector.

28. The vector of claim 26, wherein said vector is a viral vector.

29. The vector of claim 28, wherein said viral vector is selected from the group consisting of adenovirus, herpesvirus, Epstein-Barr virus, and baculovirus vectors.

30. The vector of claim 29, wherein said viral vector is an adenovirus vector.

31. The vector of claim 29, wherein said viral vector is a herpesvirus vector.

32. The vector of claim 26, wherein said vector further comprises the adenovirus 5' and 3' cis elements required for adenovirus replication and encapsidation.

33. The vector of claim 32, wherein said vector further comprises the AAV cap coding sequences.

34. The vector of claim 26, wherein said vector further comprises the adenovirus sequences providing the helper functions essential for AAV viral infection.

35. The vector of claim 34, wherein said vector further comprises the AAV cap coding sequences.

36. The vector of claim 35, wherein said vector is a plasmid.

37. A composition comprising the nucleotide sequence of any of claim 1, 19, 22 or 23 in a physiologically-acceptable carrier.

38. A cell comprising the nucleotide sequence of any of claim 1, 19, 22 or 23.

39. The cell of claim 38, wherein said nucleotide sequence is stably integrated into the cell.

40. The cell of claim 38, wherein said cell is selected from the group consisting of a bone cell, neural cell, retinal cell, lung cell, epithelial cell, muscle cell, pancreatic cell, hepatic cell, myocardial cell, dendritic cell, progenitor cell, stem cell, spleen cell, keratinocyte, fibroblast, endothelial cell, and germ cell.

41. A pharmaceutical formulation comprising the cell of claim 38 in a pharmaceutically-acceptable carrier.

42. The nucleotide sequence of claim 1 further comprising a mutation selected from the group consisting of:

(a) a missense mutation at the p19 start site, (b) a missense mutation at the 5' splice donor site; and (c) a missense mutation at the p19 start site and 5' splice donor site.

* * * * *

UNITED STATES PATENT AND TRADEMARK OFFICE
CERTIFICATE OF CORRECTION

PATENT NO. : 6,627,617 B1
DATED : September 30, 2003
INVENTOR(S) : Samulski et al.

It is certified that error appears in the above-identified patent and that said Letters Patent is hereby corrected as shown below:

<u>Title page,</u>
Item [73], Assignee should appears as follows:
-- University of North Carolina at Chapel Hill, Chapel Hill, NC (US)
   Univesrity of Florida, Gainesville, FL (US) --

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,627,617 B1
DATED : September 30, 2003
INVENTOR(S) : Samulski et al.

It is certified that error appears in the above-identified patent and that said Letters Patent is hereby corrected as shown below:

Title page,
Item [73], Assignee should appears as follows:
-- University of North Carolina at Chapel Hill, Chapel Hill, NC (US)
   University of Florida, Gainesville, FL (US) --

This certificate supersedes Certificate of Correction issued June 1, 2004.

Signed and Sealed this

Twenty-fourth Day of May, 2005

JON W. DUDAS
*Director of the United States Patent and Trademark Office*